(12) United States Patent
Freeman et al.

(10) Patent No.: US 11,794,027 B2
(45) Date of Patent: Oct. 24, 2023

(54) ACTIVE COMPRESSION DECOMPRESSION RESUSCITATION INTEGRATED TREATMENT SYSTEM

(71) Applicant: ZOLL Medical Corporation, Chelmsford, MA (US)

(72) Inventors: Gary A. Freeman, Waltham, MA (US); Keith Lurie, Minneapolis, MN (US); Anja Metzger, Lake Elmo, MN (US); James R. Homuth, Corcoran, MN (US)

(73) Assignee: ZOLL Medical Corporation, Chelmsford, MA (US)

( * ) Notice: Subject to any disclaimer, the term of this patent is extended or adjusted under 35 U.S.C. 154(b) by 1283 days.

(21) Appl. No.: 16/280,212

(22) Filed: Feb. 20, 2019

(65) Prior Publication Data
US 2019/0255340 A1 Aug. 22, 2019

Related U.S. Application Data

(60) Provisional application No. 62/633,175, filed on Feb. 21, 2018.

(51) Int. Cl.
| | |
|---|---|
| *A61N 1/00* | (2006.01) |
| *A61N 1/39* | (2006.01) |
| *A61N 1/04* | (2006.01) |
| *A61B 5/1455* | (2006.01) |
| *A61B 5/083* | (2006.01) |
| *A61H 31/00* | (2006.01) |

(Continued)

(52) U.S. Cl.
CPC .......... *A61N 1/3925* (2013.01); *A61B 5/0836* (2013.01); *A61B 5/14552* (2013.01); *A61B 5/318* (2021.01); *A61B 5/339* (2021.01); *A61H 31/005* (2013.01); *A61M 16/0078* (2013.01); *A61N 1/046* (2013.01); *A61N 1/3918* (2013.01); *A61N 1/3931* (2013.01); *A61N 1/39044* (2017.08); *A61N 1/3968* (2013.01); *A61N 1/3993* (2013.01); *A61B 2562/0219* (2013.01); *A61H 2201/10* (2013.01)

(58) Field of Classification Search
CPC .......................... A61N 1/3925; A61N 1/39044
USPC .......................................................... 601/41
See application file for complete search history.

(56) References Cited

U.S. PATENT DOCUMENTS

| | | | |
|---|---|---|---|
| 7,440,335 B2 | 10/2008 | Ramaraju | |
| 2018/0256446 A1* | 9/2018 | Tan | ...................... A61H 31/005 |

FOREIGN PATENT DOCUMENTS

WO    WO 2016154425    9/2016

* cited by examiner

*Primary Examiner* — Nicole F Lavert
(74) *Attorney, Agent, or Firm* — Mintz Levin Cohn Ferris Glovsky and Popeo, P.C.

(57) ABSTRACT

A medical apparatus provides resuscitative therapy to a patient. The apparatus includes an electrocardiogram (ECG) input, a defibrillation output configured to provide an electrical defibrillation shock treatment, and an applicator body configured to provide active compression decompression therapy to the patient's chest. The applicator body includes a rescuer end configured for hands of the rescuer to press and pull on the applicator body, a coupling surface configured to adhere to the patient's chest to provide active compression decompression therapy, a capacitor, and processor(s) configured to receive and analyze the ECG signal of the patient, determine whether the patient is in need of defibrillation, and administer the defibrillation shock treatment to the patient.

46 Claims, 16 Drawing Sheets

(51) Int. Cl.
*A61M 16/00* (2006.01)
*A61B 5/318* (2021.01)
*A61B 5/339* (2021.01)

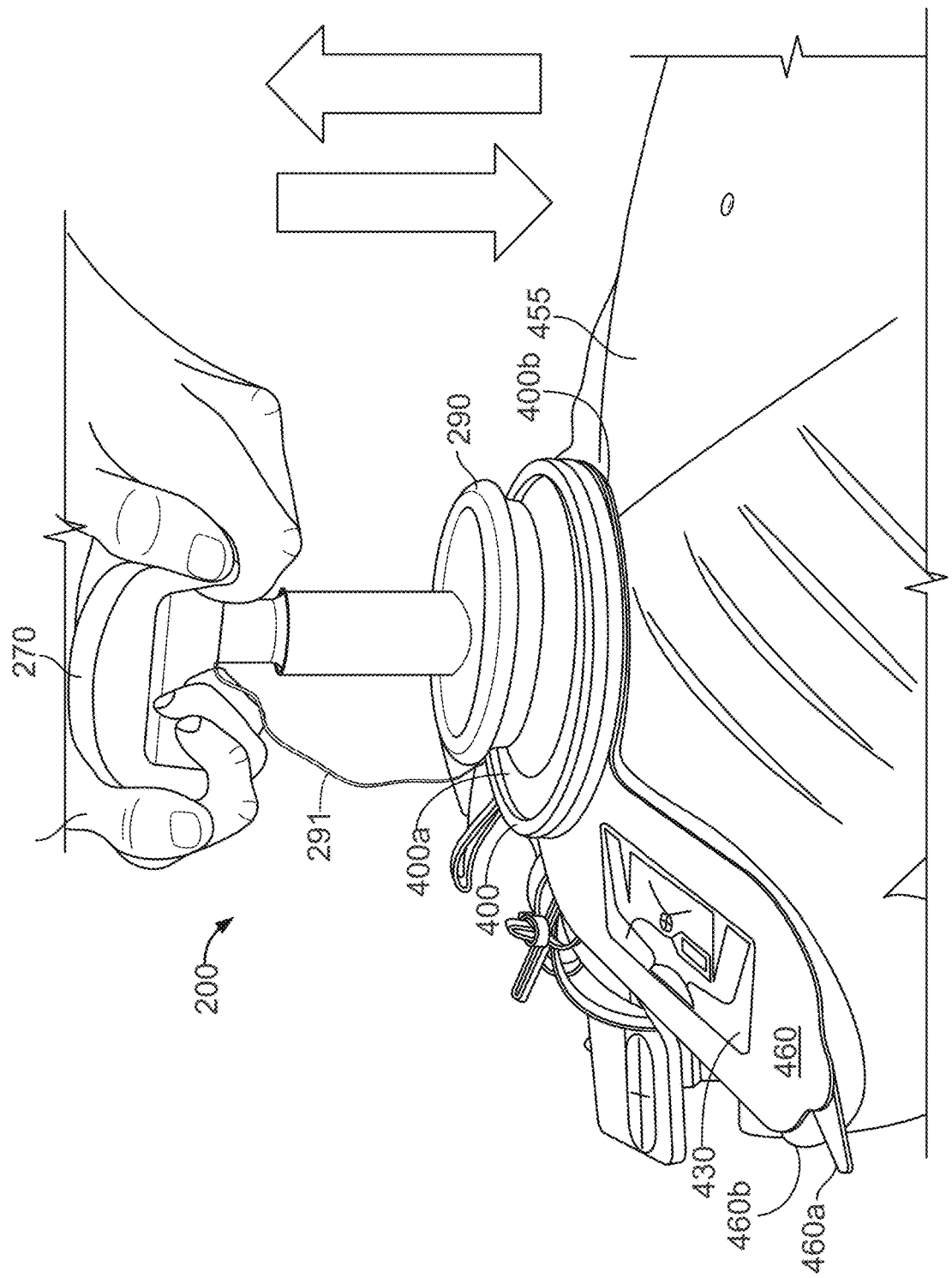

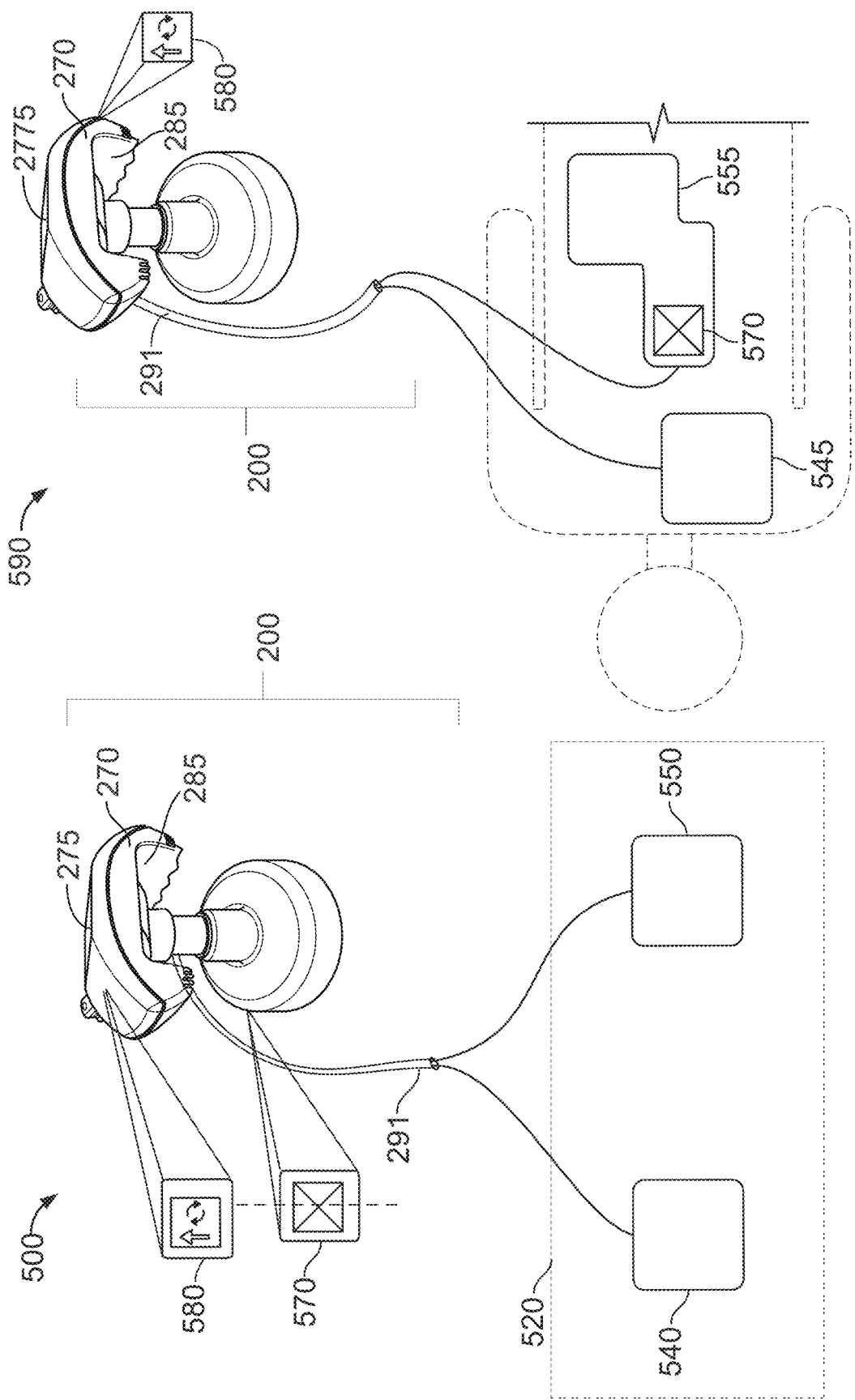

ACTIVE COMPRESSION DECOMPRESSION RESUSCITATION INTEGRATED TREATMENT SYSTEM

CLAIM OF PRIORITY

This application claims priority under 35 U.S.C. § 119(e) to U.S. Patent Application Ser. No. 62/633,175, filed on Feb. 21, 2018, the entire contents of which are hereby incorporated by reference.

TECHNICAL FIELD

This document relates to cardiac resuscitation systems and techniques and in particular to systems and techniques for assisting rescuers in performing and optimizing Cardio-Pulmonary Resuscitation (CPR) and Electrocardiogram (ECG) measurements.

BACKGROUND

Treating a patient undergoing a cardiac arrest typically requires multiple therapies. For situations where the patient has been in cardiac arrest for more than a minute or two, typically CPR, and in particular chest compressions, is the first recommended therapeutic intervention, followed by more advanced interventions such as electrical defibrillation and ventilator support of the patient. CPR is a process by which one or more rescuers can provide chest compressions and/or ventilation to a patient who has suffered a cardiac arrest. Chest compressions are considered to be the most important element of CPR during the first five to eight minutes after CPR efforts begin, because chest compressions help maintain circulation through the body, heart, and brain, which are the organs that can sustain the most damage from an adverse cardiac event. Many factors, such as the depth of chest compression, the location of the applied pressure, and the timing of the chest compressions, can affect the outcome of CPR. Active Compression Decompression (ACD) is a type of chest compression that involves both the conventional downward compression on the patient's sternum, followed by pulling upward on the patient's sternum during the decompression phase, with the pulling force typically via a suction cup or other adhering coupling element attached to a handle that is pulled upward by the rescuer during the decompression phase. The active decompression phase of ACD results in better venous refilling of the heart, and thus enhanced blood flow during chest compressions.

SUMMARY

This document describes a medical apparatus that includes an electrocardiogram (ECG) input configured to receive an ECG signal of the patient, a defibrillation output configured to provide an electrical defibrillation shock treatment to the patient, and an applicator body coupled with the ECG input and the defibrillation output and configured to provide active compression decompression therapy to the patient's chest. The applicator body includes a rescuer end configured for hands of the rescuer to press and pull on the applicator body, a coupling surface configured to adhere to the patient's chest to provide active compression decompression therapy as the rescuer presses and pulls on the applicator body, at least one capacitor configured to store charge for applying a defibrillation shock treatment to the patient, and one or more processors. The one or more processors are configured to receive and analyze the ECG signal of the patient from the ECG input, determine, based on analysis of the ECG signal, whether the patient is in need of defibrillation, and administer the defibrillation shock treatment to the patient via the defibrillation output based on the determination of whether the patient is in need of defibrillation.

In some implementations, the medical apparatus includes at least one chest compression sensor for monitoring one or more chest compression parameters. The one or more chest compression parameters can include at least one of a displacement parameter, a force parameter, and a velocity parameter. In some implementations, the at least one chest compression sensor can include at least one of a motion sensor and a force sensor. In some implementations, the motion sensor includes at least one of an accelerometer, a velocity sensor and a displacement sensor.

In some implementations, the medical apparatus includes at least one electrode configured to be coupled with the ECG input and adhered to at least a portion of the patient's chest for monitoring the ECG of the patient. In some implementations, the at least one electrode is coupled with the defibrillation output and transmits the defibrillation shock treatment to the patient from the at least one capacitor. In some implementations, the at least one electrode is coupled with the defibrillation output and transmits the defibrillation shock treatment to the patient from the at least one capacitor. In some implementations, the at least one electrode is configured to deploy a conductive gel to adhere to a portion of the chest of the patient. In some implementations, an electrode is a deployable electrode configured to be adhered to a portion of a back of the patient. In some implementations, the deployable electrode is configured to be deployed from the applicator body using a spring-loaded mechanism. In some implementations, the deployable electrode includes a semi-rigid plate electrode.

In some implementations, the one or more processors are configured to determine whether the ECG signal comprises a shockable or non-shockable rhythm, and cause the at least one capacitor and the at least one electrode to apply the defibrillation shock treatment upon a determination that the ECG signal comprises a shockable rhythm. In some implementations, the one or more processors are configured to detect chest compressions being administered to the patient for the resuscitative treatment. In some implementations, the one or more processors are configured to transmit a feedback signal for assisting a user in administering the chest compressions. In some implementations, the one or more processors are communicatively coupled with a computing device including at least one of a tablet, a server, phone, a watch, laptop, and a mobile computing device. In some implementations, the one or more processors transmit patient data to the computing device, and the patient data includes information indicative of at least one of the ECG signal and the administered defibrillation shock treatment.

In some implementations, the medical apparatus includes a user interface that provides, by an output device, one or more of cardio-pulmonary resuscitation (CPR) instructions and defibrillation instructions, where the instructions include treatment data from one or more sensors.

In some implementations, the applicator body includes an insulating material configured to electrically isolate a defibrillating shock of the defibrillation shock treatment. In some implementations, the coupling surface of the applicator body couples to the chest of the patient using one or more of an adhesive, one or more suction cups, and/or a gel. In some implementations, the applicator body includes a stem disposed between the rescuer end and the coupling surface, and the stem houses the at least one capacitor.

In some implementations, transmitting the signal for administration of the resuscitative treatment includes synchronizing a defibrillating shock treatment with a chest compression cycle.

Among the advantages of the integrated treatment system, the integrated treatment system enables a rescuer to perform CPR treatment to a patient using active compression and decompression treatment (hereinafter "ACD treatment"), such as using the applicator body of the integrated treatment system. The CPR treatment can be performed while monitoring an ECG signal of the patient and chest compression parameters from sensors attached to the patient such that the rescuer receives instantaneous feedback regarding the status of the patient during treatment. The one or more electrodes of the treatment system enable the rescuer to deliver a defibrillating shock to the patient without having to remove the active compression-decompression device of the integrated treatment system.

Integration of the active compression and decompression device with the one or more electrodes minimizes delay between compression cycles caused by defibrillation treatment. For example, once the defibrillating shock has been delivered by the integrated treatment system, the system is immediately ready for compressions using ACD treatment to be performed, either automatically or by the rescuer, without the rescuer having to reconfigure, replace, or position the applicator body to the patient.

In some implementations, the integrated treatment system can monitor an ECG signal while ACD treatment is being performed. For example, the integrated treatment system can be calibrated to account for compression artifacts in the ECG signal. For example, when the ACD treatment is automated, the integrated treatment system can be calibrated using the known parameters of the ACD treatment to calibrate the ECG signal for later analysis during defibrillation treatment. For example, the integrated treatment system may determine that the calibrated ECG signal indicates a shockable rhythm, while the raw ECG signal may indicate a non-shockable rhythm due to ACD treatment artifacts. For example, the integrated treatment system can synchronize defibrillation treatment and ACD treatment of the patient.

Other features and advantages will be apparent from the description, from the drawings, and from the claims.

DESCRIPTION OF DRAWINGS

FIGS. 4A-4C show examples of the integrated treatment system positioned on a patient.

FIGS. 5A-5B show examples of the ACD Resuscitation device and electrode assemblies.

DETAILED DESCRIPTION

Figure 1:
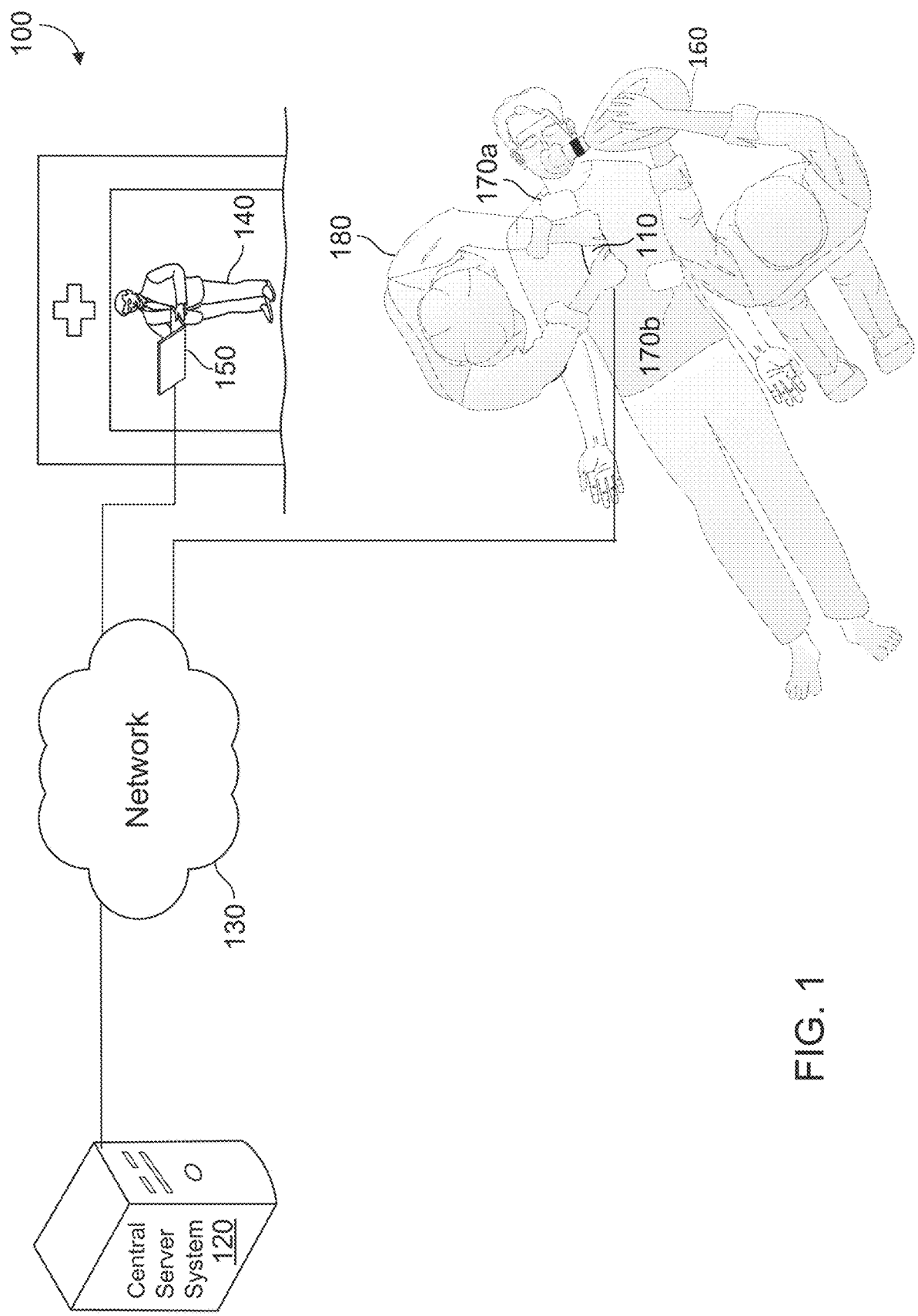
FIG. 1 shows an overhead view of rescuers providing resuscitative treatment to a patient an integrated treatment system.

Implementations of the present disclosure are generally directed to an integrated treatment system for managing medical treatment, including both cardiopulmonary resuscitation (CPR) and defibrillation treatment, to a patient in need of emergency assistance, such as a patient suffering of cardiac arrest. Active compression-decompression CPR (hereinafter "ACD CPR") differs from standard CPR in that it actively re-expands (decompresses) the chest after each compression. Due to the time-sensitive nature of acute care resuscitation, ACD CPR is more effective when compression and decompression cycles are performed with fewer pauses during the course of the treatment. Pauses are likely to occur when switching between devices, for example, removing an ACD device from the patient's chest so that a defibrillation system may be properly placed, or vice versa.

In some implementations, using systems and device according to the present disclosure, a rescuer can monitor an electrocardiogram (ECG) signal of the patient and/or initiate and perform defibrillation treatment, such as electric shock therapy, using the integrated treatment system. The rescuer can also perform treatment using the integrated treatment system having fewer pauses in ACD CPR treatment for monitoring ECG signals or applying an electric shock, for example as compared to when the ACD device is provided separately from a defibrillator/monitor. In particular, implementations of the present disclosure are generally directed to systems for assisting a rescuer to perform ACD CPR in conjunction with defibrillating shock therapy using the integrated treatment system, with minimum delay in providing either and/or different types of treatment.

For performing an ACD CPR treatment, a rescuer can attach (e.g., by using an adhesive pad, suction cup, etc.) an applicator body of the integrated treatment system to the patient's chest and apply force to the patient's chest during multiple phases of ACD CPR treatment. For example, during a compression phase, a rescuer can press down on the applicator body of the system with sufficient force to compress the patient's chest and induce arterial blood circulation by ejecting blood from cardiac chambers. During an active decompression phase, the rescuer can pull up on the applicator body of the system so that the applicator body of the system pulls on and expands the patient's chest, enabling cardiac chambers to refill with blood and, in some cases, assist in ventilating the patient's lungs. The downward and upward strokes can be monitored and repeated at a controlled magnitude and rate to optimize blood circulation and/or enhance ventilation. For example, the compression magnitude can be in a range from about 3.5 cm to about 5 cm and the compression rate can be in a range from about 60 compressions to about 100 compressions per minute.

The integrated treatment system used for ACD CPR treatment can include an ECG input for receiving an ECG signal from the patient and a defibrillation output for transmitting an electrical defibrillation shock to the patient. The ECG input includes a port (e.g., a physical connection port) for receiving the ECG signal. The integrated treatment system may further include one or more electrodes that are configured to be adhered to a portion of the patient. The one or more electrodes can be coupled with the ECG input for monitoring an ECG signal from the patient. In some implementations, the electrode(s) can be coupled with the defibrillation output for applying an electric shock therapy, as controlled or otherwise provided from an ACD Resuscitation device that has defibrillation capability. The defibrillation output includes a port, which can be the same port as the ECG input or be distinct from the ECG input. In some embodiments, the electrodes used for receiving ECG information from the patient and providing ECG signals to the ECG input are the same electrodes that are in communication with the defibrillation output and used to provide the defibrillation shock treatment to the patient (e.g., when the ECG input and defibrillation output include a shared port). In other embodiments, there may be electrodes dedicated to the ECG input and providing ECG information from the patient to the ECG input, and other electrodes dedicated to the defibrillation output and providing electrical defibrillation treatment to the patient. For example, there may be a 12-lead ECG where there are more than 2 ECG leads placed at locations different from the defibrillation electrodes. In such a case, the ECG input includes a port that is separate from the defibrillation output. In some implementations, the parts of the defibrillator can be a part of the applicator body of the ACD Resuscitation device. Applying both ACD CPR treatment in conjunction with one or more aspects of resuscitation, such as using the ECG signal of the patient (e.g., for electrotherapy including defibrillation and/or pacing) can be referred to as ACD Resuscitation treatment. Details regarding various implementations of the integrated treatment system and one or more methods of using the integrated treatment system are described in further detail with reference to FIGS. 1-11.

FIG. 1 shows an example of an integrated treatment system 100 for providing resuscitative treatment. The integrated treatment system 100 includes devices for performing ACD treatment, ECG signal monitoring and other treatment feedback, and defibrillation treatment. The integrated treatment system 100 includes an external chest active compression and decompression (ACD) and defibrillation device 110 (hereinafter "the ACD Resuscitation device"). The ACD Resuscitation device 110 includes features that support both ACD CPR treatment functionality and defibrillation functionality. For example, the ACD Resuscitation device 110 includes an automated external defibrillator (AED) that can be connected to one or more electrodes (e.g., electrodes 170a, 170b) for defibrillation treatment of a patient. In such a case, the one or more electrodes may be communicatively coupled with the defibrillation output (e.g., connector 220a of FIG. 3B) of the ACD Resuscitation device for providing the electrical defibrillation shock to the patient. The ACD Resuscitation device 110 is configured to synchronize both ACD CPR treatment and defibrillation. For example, the ACD Resuscitation device 110 is configured to monitor ECG data using one or more electrodes on the patient during ACD CPR (or other types/aspects of CPR) treatment of the patient and recommend defibrillation shock treatment as appropriate. In this instance, the one or more electrodes may be communicatively coupled with the ECG input (not shown) of the ACD Resuscitation device 110 for monitoring the ECG of the patient. As discussed above, the same electrode(s) that are used for monitoring the ECG of the patient may also be used for defibrillation of the patient. Though, in other cases, different electrodes may be used for monitoring ECG of the patient and providing a defibrillation shock to the patient. That is, ECG electrodes may be used to provide ECG information to the ECG input of the ACD Resuscitation device 110, and separate defibrillation electrodes may be used to provide a defibrillation shock to the patient from the defibrillation output (e.g., a portion of connector 220a) of the ACD Resuscitation device 110. If one or more processor(s) of the ACD device analyze the ECG data and indicate that the ECG qualifies as a shockable rhythm of the patient during ACD CPR or during pauses between ACD CPR, the rescuer may be instructed to cease ACD CPR treatment (if the indication occurs during the ACD CPR) and activate a shock therapy of the ACD Resuscitation device 110.

Figure 3A:
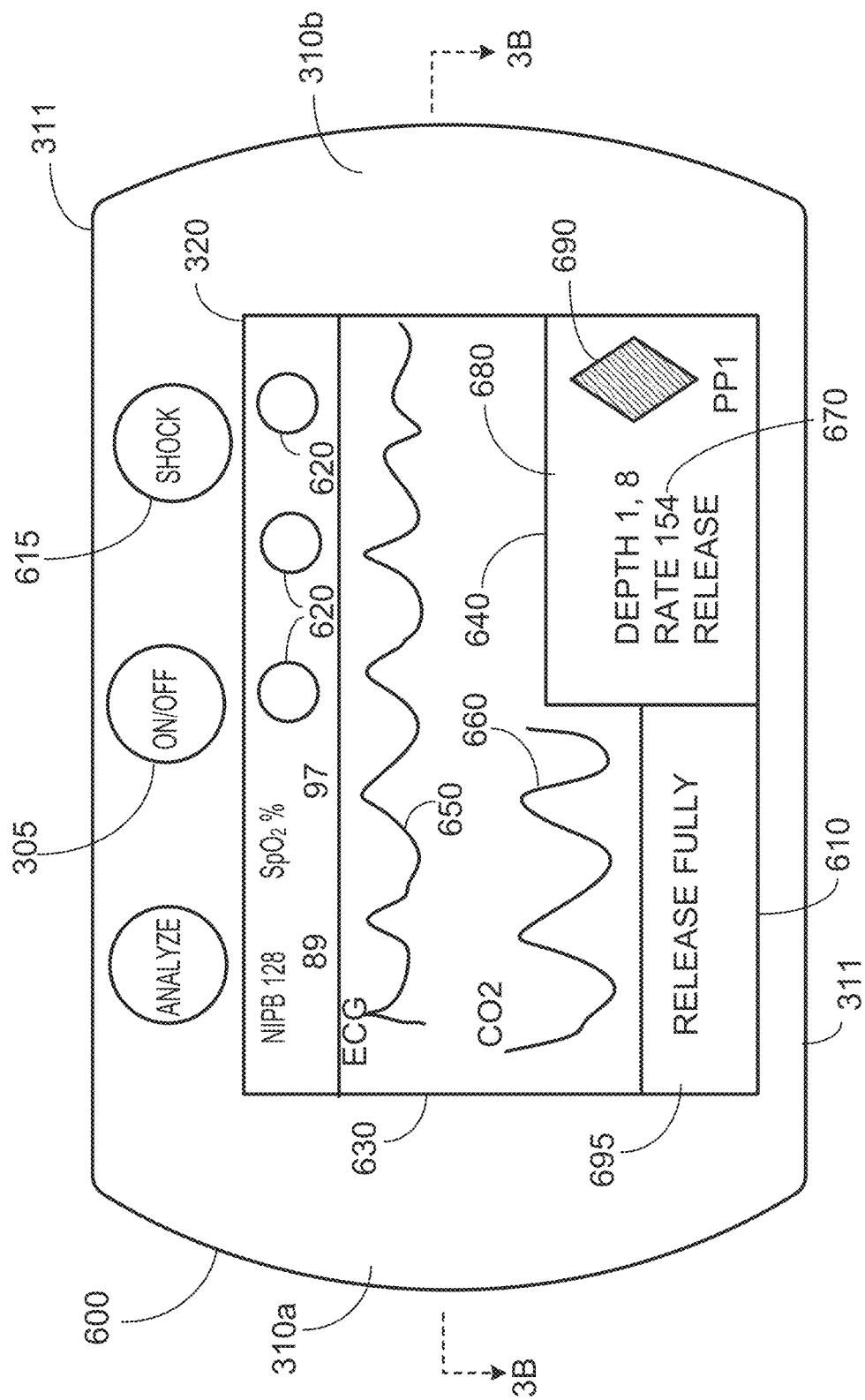
FIGS. 3A and 3B show top and cross-sectional views of an example ACD Resuscitation device and a portion of the integrated treatment system.
Figure 3B:
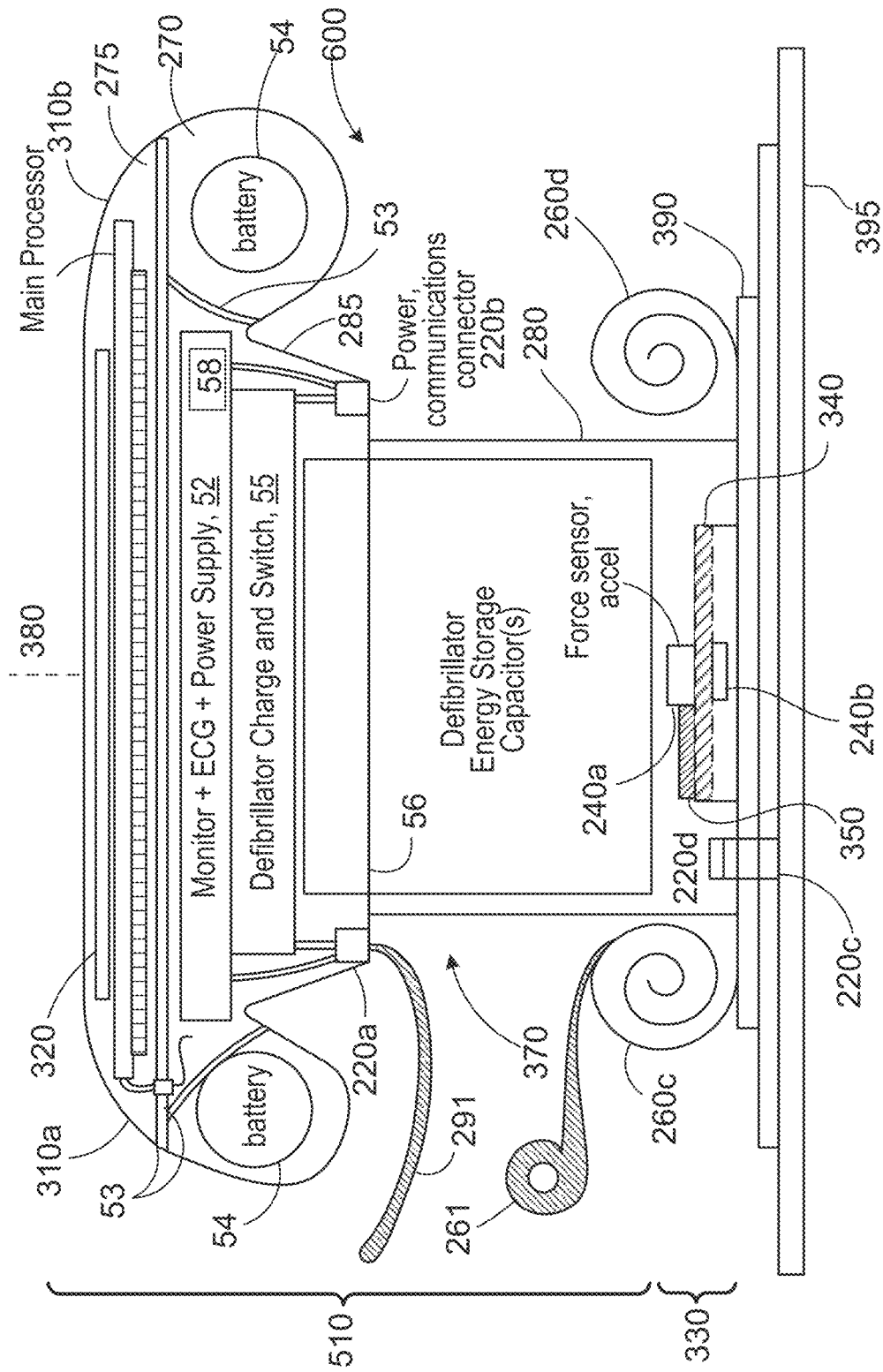
Figure 10:
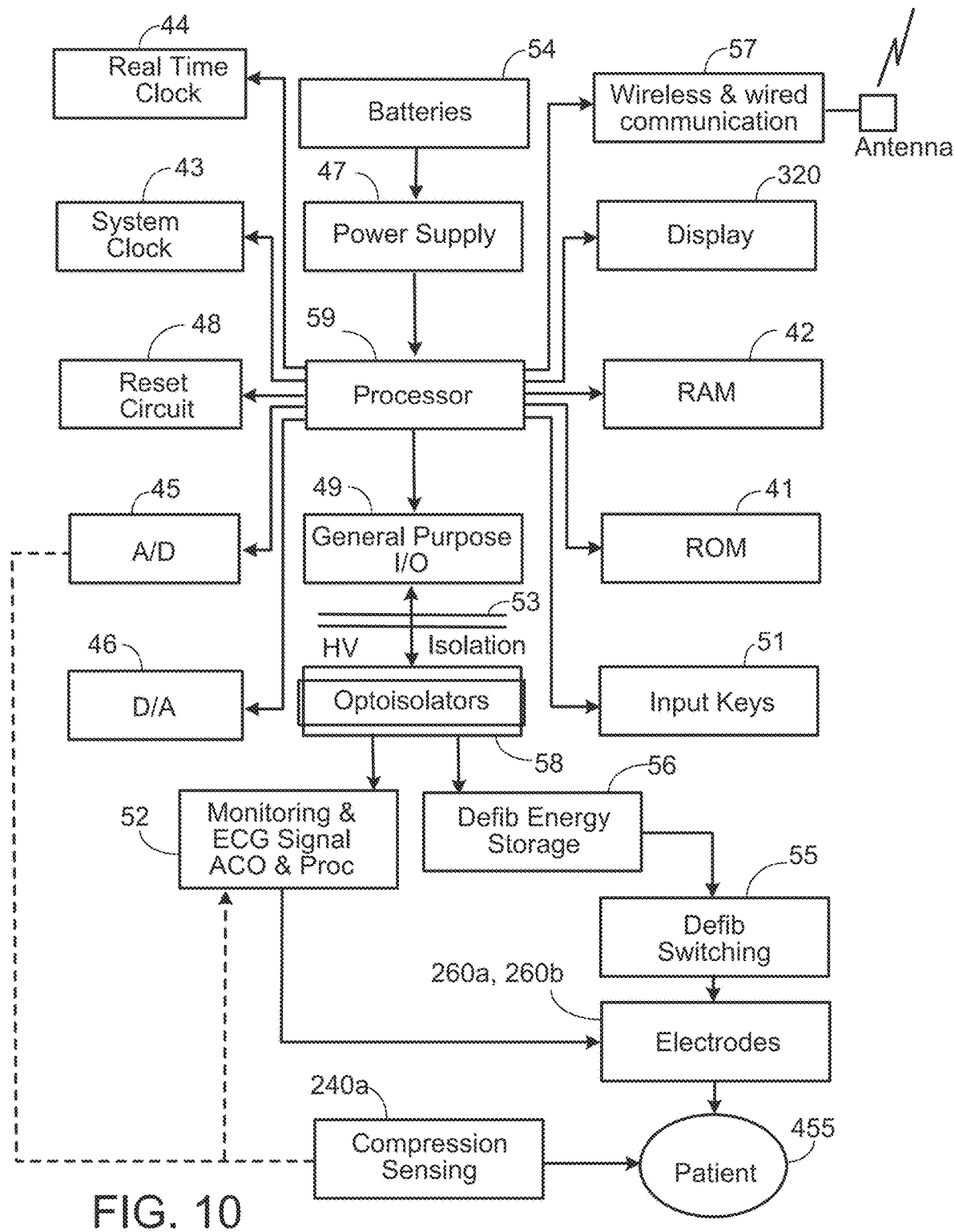
FIG. 10 shows a block diagram of the defibrillator/ECG system used in the ACD Resuscitation device
Figure 11:
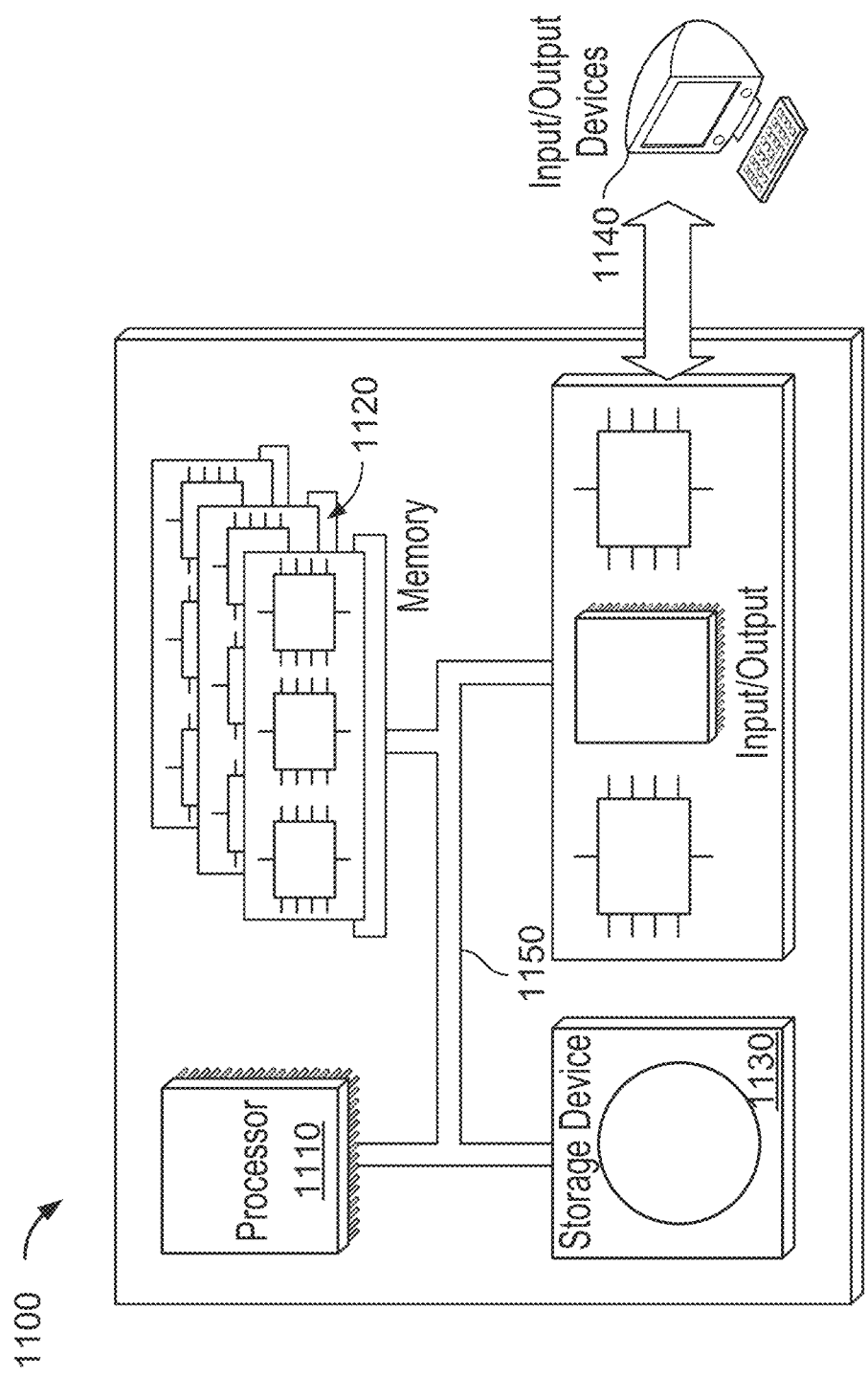
FIG. 11 shows a computing system such as for an example ACD Resuscitation device.

Referring to FIGS. 10 and 3B, in some implementations, the areas of the ACD Resuscitation device 110 gripped by the rescuer are electrically isolated from the high voltage components and circuitry, such as with electrical insulation 53 like plastics and other dielectrics and proper creepage and clearance distances or optoisolators 58, to enable the rescuer to continue CPR compressions and decompressions contemporaneous with delivery of a defibrillation shock. Such electrical isolation is provided for protection of the rescuer from the defibrillation shock. More detail regarding synchronized treatment is described below.

In some implementations, the ACD Resuscitation device 110 can be connected to a network 130 to transmit the acquired data to a remote computing device that can be operated by remote medical personnel. The CPR and ECG data transmitted by the ACD Resuscitation device 110 to the remote computing device can include data associated to the performance of the rescuer and data associated to the response of the patient to CPR treatment and defibrillation shock therapy. The ACD Resuscitation device 110 can send (e.g., transmit) data about the performance of chest compressions and decompressions, such as depth and rate data for the chest compressions and decompressions. The ACD Resuscitation device 110 can send ECG traces to the remote computing device. In some implementations, the ACD Resuscitation device 110 sends the ECG trace and compression and decompression data that have a common timeline so that a complete record of the ACD Resuscitation treatment can be analyzed by the remote computing device. In some implementations, the ACD Resuscitation device 110 can first calibrate the ECG signal based on the compression and decompression data that has been received and then send the calibrated ECG signal to the remote computing device. The ACD Resuscitation device 110 can also send data from the other sensors of the integrated treatment system 100 or from sensors associated with the patient and attached to or otherwise in communication with the ACD Resuscitation device 110, such as an airflow sensor attached to a ventilation bag.

A central server system 120 can communicate with the remote computing device, ACD Resuscitation device 110, or other devices of the integrated treatment system 100, such as at the rescue scene over a wireless network and/or other network (e.g., network 130), which can include portions of the Internet (where data can be appropriately encrypted to protect privacy). The central server system can be provided as a server, or a virtual server, that runs server software components, and can include data storage including, but not limited to, a database and/or flat files. The central server system can be part of a larger system of a healthcare continuum, in which patient data and rescuer profiles are stored. Patient data can be associated with an identification number or other identifier, and stored by the central server system for later access. For example, ECG data, ACD data, or both, can be sent to the central server and stored in a patient log, along with timestamp data, device identifiers of the ACD Resuscitation device 110 or other equipment used, and so forth.

Additionally, the central server system can store rescuer profiles that include default rescuer profiles and rescuer specific profiles associated with particular rescuers. A rescuer specific profile associated with a particular rescuer can be retrieved by using an identification number or other identifier, stored by the central server system 120 for later access. The rescuer specific profiles can include template positions and data extracted from past rescue attempts, in which the rescuers participated. The data extracted from past rescue attempts can include rescuer's performance during CPR treatment or ACD Resuscitation treatment. For example, the rescuer's performance during CPR can include rescuer's skill level in performing CPR treatment, indicators of rescuer fatigue level, duration of CPR, and success of CPR treatment.

The central server system stores treatment data that is accessible by users such as rescuers, medical personnel (e.g., personnel 140), etc. For example, a user, operating a computing device 150 that communicates wirelessly, such as over a cellular data network can access current and past CPR and ECG data. As such, the user can review CPR and associated ECG data stored in the central server system. In this manner, the integrated treatment system 100 permits various portable electronic devices to communicate with each other so as to coordinate and optimize care that is provided to a patient based on the profiles of the available rescuers at the rescue scene. In such examples, the integrated treatment system 100 could be configured to optimize CPR and defibrillation treatment by providing optimal chest compressions and decompressions for shorter periods of time than the complete CPR duration and initiating defibrillation of the patient, such as monitoring the ECG signal or initiating a defibrillating shock. In addition, the integrated treatment system 100 enables the rescuers and other medical personnel to access real-time data and optimized real-time and/or historical data associated with ACD Resuscitation and defibrillation treatment.

The integrated treatment system 100 can include other components to assist the rescuer during ACD Resuscitation treatment. For example, a visual metronome can guide the rescuer to compress and decompress the chest of the patient at the appropriate rate and force. The ACD Resuscitation device 110 can be a standalone device that is placed on the patient's chest (e.g., as illustrated in FIGS. 3A-3B). The ACD Resuscitation device 110 can also be attached to another device used by the rescuer or other medical personnel during treatment, such as an external monitor, mobile phone, network gateway, and so forth. For example, a mobile phone can be connected to the integrated treatment system 100, in which visual feedback, such as a graphical user interface that displays an ECG trace, compression timing and depth measurements, or other feedback of the ACD Resuscitation treatment, can be provided to the rescuer from a location that is away from the ACD Resuscitation device 110. The attachment of the ACD Resuscitation device 110 with other devices can enable synchronization of multiple CPR-related procedures.

In some implementations, the integrated treatment system 100 can include additional therapeutic delivery devices for delivering the appropriate therapy to the patient. The therapeutic delivery devices can be, for example, a drug infusion device, an automatic ventilator and/or a device that includes multiple therapies such as defibrillation, chest compression, ventilation, and drug infusion. The therapeutic delivery devices are physically separate from the ACD Resuscitation device 110, and control of the therapeutic delivery devices can be accomplished by a communications link from the ACD Resuscitation device 110 that can be wired, wireless, or both. For example, a ventilation bag 160 is shown.

In some implementations, the rescuer (e.g., rescuer 180) can be a lay rescuer who was in the vicinity of the patient when the patient required care, or can be trained medical personnel, such as emergency medical personnel (EMTs). Additional rescuers can also care for the patient, and can be included in a rotation of rescuers providing particular components of care to the patient, where the components can include chest compressions, ventilation, administration of drugs, and other provisions of care along with and in addition to use of the integrated treatment system 100.

Figure 2:
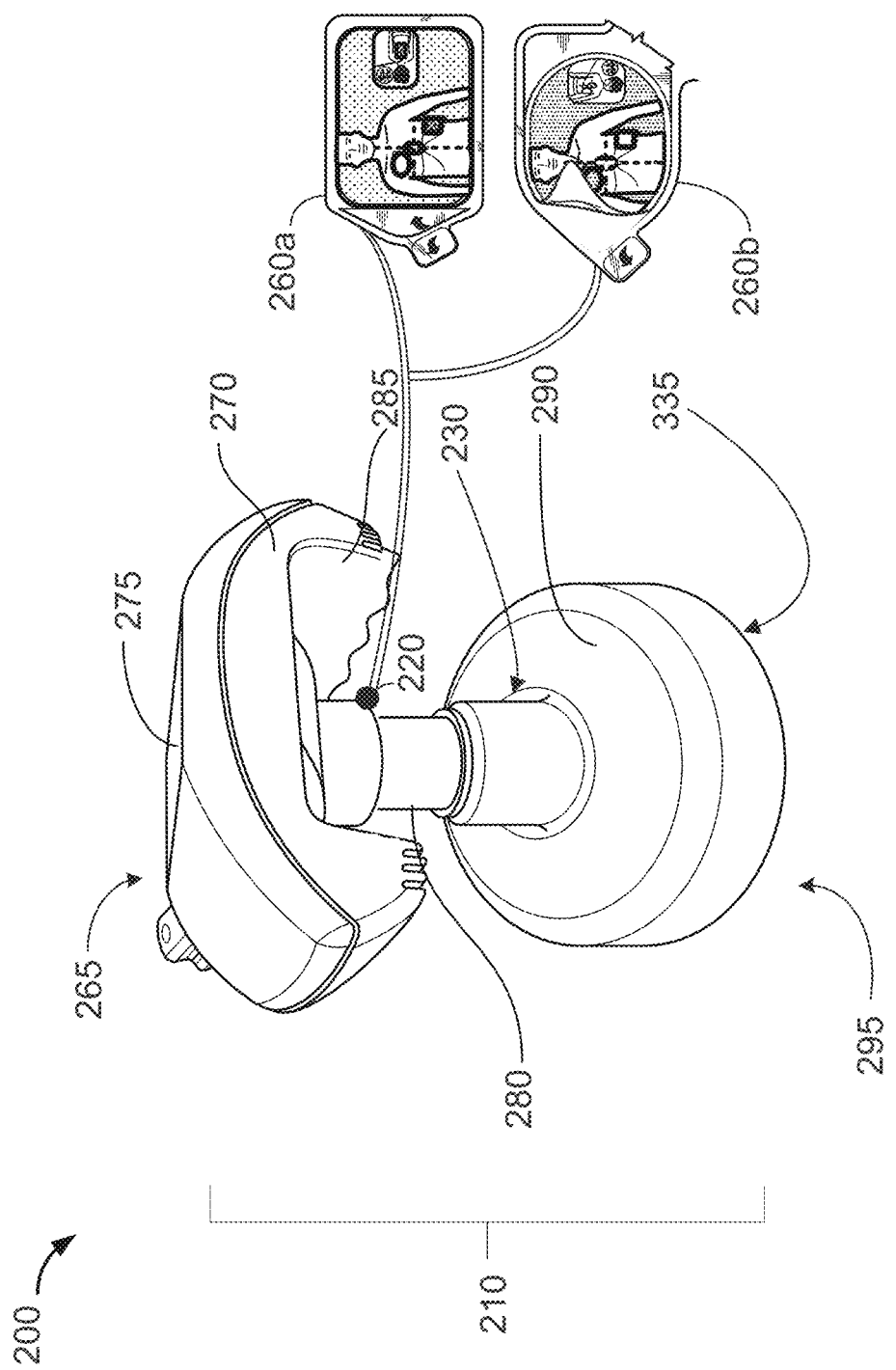
FIG. 2 shows a perspective view of an ACD Resuscitation device.

FIG. 2 illustrates examples of components of an ACD Resuscitation device 200 (e.g., ACD Resuscitation device 110 of FIG. 1) of the integrated treatment system 100. The example components of the ACD Resuscitation device 200 can include an applicator body 210, a sensor package 230, a coupling mechanism 290, and electrodes 260a, 260b electrically and/or communicatively coupled to the ECG input (e.g., connector 220b of FIG. 3B) and/or defibrillation output (e.g., a portion of connector 220a of FIG. 3B) of the ACD Resuscitation device 200.

The ACD Resuscitation device 200 includes the applicator body 210 having a rescuer end 265 and a patient end 295. The applicator body 210 serves as a mechanical base for performing ACD compressions and decompressions, such as by a rescuer, and serves as housing for one or more other components of the ACD Resuscitation device 200. The applicator body 210 forms a rigid or semi-rigid chassis. The applicator body 210 provides a mechanical coupling for application of compression and decompression forces on a patient by a rescuer. In some implementations, the applicator body 210 can be shaped as an elongated cylinder or prism, such as a tubular shape. The ACD Resuscitation device 200 includes, in addition to the applicator body 210, a handle 270, a stem 280, and coupling mechanism 290 having a surface for coupling with the patient. The handle 270 is attached to a rescuer end 265 of the applicator body 210, and the coupling mechanism 290 is attached to a patient end 295 of the applicator body 210 via the stem 280. The rescuer end 265 of the applicator body 210 is at a location distal to the patient and is the portion of the applicator body with which the rescuer engages to provide active compression decompression to the patient. The patient end 295 of the applicator body 210 is at a location proximal to the patient, having a coupling surface and/or mechanism for coupling with the patient so that the applicator body is able to press and pull up on the patient for the administration of active compression decompression (ACD) therapy. For example, the rescuer end 265 may include a handle, strap or other structure where the rescuer can hold and/or exert a pushing or pulling force on the applicator body in respective directions toward or away from the patient. The coupling mechanism 290 of the patient end 295 may include a suitable mechanism for binding, attaching, adhering or otherwise engaging with the chest of the patient. Accordingly, when the patient end 295 is appropriately coupled to the patient's chest and the rescuer exerts a pulling force on the applicator body, the patient's chest is effectively pulled upward so as to create a negative intrathoracic pressure in the thorax, for enhancing circulation within the body (e.g., assisting venous return of blood back to the heart).

The applicator body 210 forms a chassis for the ACD Resuscitation device 200 and houses one or more components of the ACD Resuscitation device 200, such as defibrillation components. The applicator body 210 forms a mechanical coupling for the rescuer to apply compression and decompression force to the patient during ACD Resuscitation treatment. The applicator body 210 connects to a rescuer end 265 (e.g., handle 270) of the ACD device that a rescuer can grasp for applying compression and decompression forces on the patient with the integrated treatment system. The applicator body 210 connects to a coupling mechanism 290 of the ACD Resuscitation device 200. The coupling mechanism 290 forms an interface for adhering the ACD Resuscitation device 200 to a portion of the patient's chest for performing compression and decompression treatment. In some implementations, the handle 270 of the rescuer end 265 and the coupling mechanism 290 are affixed to the applicator body 210 on opposing ends of the applicator body 210. For example, the handle 270 of the rescuer end 265 is presented on an end of the applicator body 210 that extends from the patient to which the coupling mechanism 290 adheres the ACD Resuscitation device 200 of the integrated treatment system 100. The applicator body and its internal components are described in greater detail in relation to FIG. 2, below.

The ACD Resuscitation device 200 can include one or more capacitors, microcontrollers, processors, batteries, monitors, speakers, and so forth to provide defibrillation capability during ACD Resuscitation treatment. In various embodiments, the capacitors, microcontrollers, processors, batteries, monitors, speakers may be part of, or separate from, the applicator body of the ACD Resuscitation device 200. In addition to providing defibrillation, the ACD Resuscitation device 200 can serve as a patient monitor via a variety of sensors or sensor packages. For example, electrodes 260a, 260b are connected to the ACD Resuscitation device 200 via the ECG input 220b and/or the defibrillation output 220a. Electrical shocking pulses can be provided to the electrodes by the ACD Resuscitation device 200 via the defibrillation output 220a in an effort to defibrillate the patient, such as with shock therapy. The integrated treatment system 100 measures electrocardiogram (ECG) signals from the patient using the electrodes 260a, 260b via the ECG input 220b. In this case, the electrodes 260a, 260b are able to provide both ECG monitoring and defibrillation capability, and so are communicatively coupled to both the ECG input 220b and the defibrillation output 220a of the ACD Resuscitation device 200. The ACD Resuscitation device 200 can further provide feedback in a conventional and known manner to an onsite rescuer, such as emergency medical personnel, using e.g., sound prompts, visual cues on a graphical user interface, and so forth. As described above, though the ECG input 220b and/or the defibrillation output 220a are shown as separate connectors in FIG. 4B, the ECG input 220b and the defibrillation output 220a can share a physical port when defibrillation electrodes are used that serve both a defibrillation function and an ECG function. In cases where different electrodes are used for the defibrillation function and the ECG function (e.g., in the case of a multiple-lead ECG where there are more than 2 ECG leads placed at locations different from the defibrillation electrodes), the ports 220a 220b can be separate physical ports.

The ACD Resuscitation device 200 includes a user interface (e.g., user interface 610 of FIG. 3A). The user interface can be a graphical user interface (GUI). In some implementations, the user interface is at an upper surface 275 of the handle 270. The user interface can include controls for a rescuer to interact with the ACD device, such as to input commands or otherwise control the ACD device of the integrated treatment system 100. The controls can include one or more of a soft key, button, trigger, portion of a touch screen, voice recognition sensor, and so forth. The user interface can include speakers for issuing sound cues or commands, such as defibrillation instructions, metronome sounds, voice commands, and so forth. The user interface is described in greater detail in relation to FIGS. 6-10B.

A computing device controls and coordinates the overall resuscitation treatment and the delivery of the various therapies, such as providing the ACD Resuscitation treatment. For example, the chest compressions and decompressions and the defibrillation of the patient can be optimized or calibrated based on a patient profile or a profile of the rescuer. A processor that is integrated in the ACD Resuscitation device 200 or is external to the ACD Resuscitation device coordinates treatment. For example, the computing device receives and analyzes a signal representing the force applied by the rescuer through the ACD Resuscitation device 200. The computing device retrieves and processes ECG data from the electrodes 260a, 260b. This computing device may be a component of the ACD Resuscitation device 200 (e.g., housed within the applicator body 210), or may be a device separate from the ACD Resuscitation device (e.g., tablet or other computer in communication with the ACD Resuscitation device).

In parallel with analyzing the force applied by the rescuer, the computing device processes the ECG signals and performs relevant determinations to optimize the amplitude and the frequency of the force applied by the rescuer and determine when to apply a defibrillating shock. The computing device therefor increases the success of ACD Resuscitation treatment. For example, if compressions and decompressions are being performed while an ECG signal is being measured, the integrated treatment system 100 can calibrate the ECG signal to account for and remove artifacts in the ECG signal that are introduced by the compressions and decompressions. Removing such artifacts can result in a better determination for the ACD Resuscitation device 200 of whether the measured heart rhythm is a shockable rhythm or not a shockable rhythm. For example, if a rate and/or depth of compressions is known because it has been measured by the computing device, the computing device can calibrate a received ECG signal accordingly to take the compressions and decompressions into account. For example, if the computing device receives a signal indicating that no compressions or decompressions were performed during an ECG signal measurement, the computing device does not perform calibrations on the ECG signal and the signal is used without the calibrations for determining whether to shock the patient. In some implementations, the computing device can measure the ECG signal and advise the rescuer, via the user interface, to perform compressions and decompressions, change the frequency and/or depth of compressions and decompressions, perform a defibrillating shock, or issue other instructions to the rescuer based on the ECG signal and compression data received. In some implementations, the computing device issues instructions to the rescuer to stand away from the patient while new ECG measurements are taken, such as if anomalous ECG data are received and new measurements need to be taken for determining whether to instruct the rescuer to perform a defibrillating shock.

The electrodes 260a, 260b form an electrode assembly. The electrodes 260a, 260b are attached to the patient in a standard position. The electrodes 260a, 260b, in this example, combine an electrode 260a positioned high on the right side of the patient's torso and an electrode 260b positioned low on the left side of the patient's torso. The electrodes 260a, 260b include metal contacts configured to measure ECG signals from the patient and deliver a defibrillating shock to the patient, and are controlled by the computing device of the ACD Resuscitation device 200. In some implementations, the electrodes 260a, 260b include flexible pads that are attached to the patient with an adhesive. In some implementations, the electrode 260b is a rigid or semi-rigid plate electrode that is placed under a back of the patient or stuck on the back of the patient. Other implementations of the electrodes are described below in relation to FIGS. 4A-5B.

The integrated treatment system 100 includes a sensor package. The sensor package is located on the ACD Resuscitation device 200 such that when the ACD Resuscitation device 200 is being used the sensor package is affixed to or proximate the patient's sternum. The sensor package can include an accelerometer, force sensor and/or other sensor that can be used in cooperation with the computing device in the ACD Resuscitation device 200. In some implementations, the sensor package provides measurements or other information that is used by the system to provide feedback on the quality of resuscitative treatment, and may further be used to generate an overall quality score for the chest compressions and decompressions performed using the ACD Resuscitation device 200. The quality score can indicate instantaneous quality or average quality across a time. For example, as a simplified description, signals from an accelerometer can be double integrated to identify a vertical displacement of the sensor package, and in turn of the sternum of the patient, to identify the magnitude of each chest compression and decompression. The time between receiving such input from the sensor package can be used to identify the pace at which chest compressions and decompressions are being applied to the patient.

The ACD Resuscitation device 200 is connected to the electrodes 260a, 260b via the ECG input 220b and/or defibrillation output 220a and can operate according to a standard protocol (e.g., to provide defibrillating shocks to the patient using the electrodes 260a, 260b). The ACD Resuscitation device 200 can include functionality of a professional defibrillator, such as the R SERIES, M SERIES, E SERIES, or X SERIES from ZOLL Medical Corporation of Chelmsford, Mass., or an automated external defibrillator (AED), including the AED PLUS, or AED PRO from ZOLL Medical Corporation. The defibrillator can better present data to the rescuer, such as in the form of lights, displays (e.g., display 630 of FIG. 3A), vibration components, or audible sound generators on a chest-mounted component such as an electrode or via an addressable earpiece for each of the rescuers. Such feedback, as discussed more fully below, can be provided on the ACD Resuscitation device and/or units that are separate from the main housing of the ACD Resuscitation device 200 that houses the defibrillator components. In some implementations, the ACD Resuscitation device 200 communicates feedback data about the patient and performance of the ACD device through either wired or wireless connects that are made directly with the ACD Resuscitation device or indirectly through another device or devices (e.g., via a separate computing device, handheld, tablet, chest compression monitor).

In some implementations, the ACD Resuscitation device 200 has limited functionality such that the ACD Resuscitation device performs Basic Life Support (BLS) functions. The ACD Resuscitation device 200 can interface with another defibrillator that is brought to the scene of the patient and that has Advanced Life Support (ALS) functionality. For example, the ACD Resuscitation device 200 can include a port or wireless gateway, which the other defibrillator can use to connect to the ACD Resuscitation device 200 and "take over" control of the electrodes 260a, 260b, display, or other functionality of the ACD Resuscitation device. Such interfacing capability enables a low-cost and smaller defibrillator system to be included in the integrated treatment system 100. As such, the integrated treatment system 100 can be more ubiquitous than more expensive alternatives and be on-hand for first responders to use while professional medical responders, such as emergency medical technicians, are on the way to the scene.

In some implementations, the integrated treatment system 100 provides real-time feedback to the rescuer. For example, the ACD Resuscitation device 200 or a display of a computing device can provide real-time audio-visual feedback, haptic feedback, and virtual reality support to the rescuer. The process of observing the quality of a component of the ACD treatment or defibrillation treatment, such as the quality of chest compressions and decompressions and concurrent ECG signal, can continue recursively as long as care is being provided to the patient. In some implementations, trends in the quality of a particular ECG trace related to the ACD treatment can be tracked rather than using absolute values of the ECG trace or compression and decompression data. As such, the ACD Resuscitation device 200 can distinguish situations in which a rescuer is giving poor chest compressions and decompressions, the electrodes 260a, 260b are incorrectly affixed to the patient or have come detached from the patient, defibrillation has changed the patient's ECG characteristics such that treatment has been completed, and so forth.

In some instances, the ACD Resuscitation device 200 can be adaptable to different CPR protocols. For example, the ACD Resuscitation device 200 can be programmed to execute ACD CPR protocols according to AHA general guidelines that can be personalized based on particular patient or rescuer needs or professional judgment. In such a situation, the ACD Resuscitation device 200 can be programmed with the parameters for each of the protocols, and an operator of ACD Resuscitation device 200 can select a protocol to be executed by the defibrillator components (or the protocol can have been selected by a medical director) and the protocol to be executed by the ACD Resuscitation device 200. Such a selection can occur at the time of a rescue, or at a prior time. For example, the ability to select a protocol can be differentiated based on access privileges, such as a person who runs an EMT service (e.g., a medical director of appropriate training and certification to make such a determination). A user interacting with the ACD Resuscitation device 200 can select the protocol to be followed on each of the machines operated by the service, and other users can be prevented from making particular changes, if lacking access privileges. In this manner, the ACD Resuscitation device 200 can be caused to match its performance to whatever protocol its users have been trained to.

Using the techniques described here, the ACD Resuscitation device 200 can, in addition to providing defibrillation shocks, ECG analysis, and other features traditionally provided by a defibrillator, also provide indications to optimize the data related to compression and decompression in real-time. The ACD Resuscitation device 200 can be deployed in the same manner as existing defibrillators, but can provide additional functionality in a manner that can be easily understood by trained and untrained rescuers, such as the integration of providing ECG analysis with the data received during ACD treatment.

The coupling mechanism 290 affixes the ACD Resuscitation device 200 to the patient, such as to the patient's chest. In some implementations, the coupling mechanism 290 couples with a coupling platform (not pictured) that is affixed to the patient's chest. In some implementations, the coupling mechanism 290 is made of a deformable rubberized material, and it comprises a body portion and a seal portion, which extends integrally from one end of the body portion. In some implementations, the coupling mechanism 290 has an enlarged open end and a reduced end that is attached to the handle 270 of the rescuer end 265. An enlarged open interior area or cavity is formed in the coupling mechanism 290 so that it opens outwardly through the open end, forming a "suction cup" configuration. In some implementations, the coupling mechanism 290 includes the stem 280 which forms a rigid end of the applicator body 210. The stem 280 is shaped to fit into a receiving interface of the coupling platform that is affixed to the patient. The coupling mechanism 290 and coupling platform are described in greater detail below in relation to FIGS. 4A-4E. In other implementations, the coupling surface may include an adhesive or other mechanism for adhering to the body of the patient.

The handle 270 of the rescuer end 265 forms a feature that can be grasped by a rescuer for application of compressions and decompressions on the patient. In some implementations, the handle 270 includes a dome-shaped upper surface 275 and an annular planar lower surface 285 separated by a peripheral flange. A top of stem 280 is centrally located attached to the ACD Resuscitation device 200 and a bottom of the stem 280 is centrally located on the coupling mechanism 290. The cross-section of the coupling mechanism 290 defines the dimensions of compressive/decompressive area, such as a landing pad affixed to the patient (e.g., landing pad 410 of FIG. 4A). The handle 270 is shaped to enable rescuer's hands to optimally grasp the handle 270 with the palms resting on the upper surface 275, the fingers wrapped around the ridge of the handle and the finger tips positioned against lower surface 285. Handle 270 and connective stem 280 can be constructed from a suitable rigid material, e.g. a molded plastic. Handle 270 can be filled with a gel, foam, padding or the like to enhance its shock-absorbing and distributing capability. The upper surface of the handle 270 includes a user interface (e.g., user interface 610 of FIG. 3A). The user interface, described in greater detail below, provides feedback related to ACD CPR treatment and defibrillation, such as to the rescuer. Other shapes of the handle 270 that permit the rescuer to perform ACD CPR treatment are conceivable.

The applicator body 210 houses a connection interface 220. As seen in FIG. 3B, the connection interface 220 includes connector 220a for one or more electrodes of an electrode assembly, such as electrodes 260a, 260b, and connection interface 220b to electrically connect electronics such as the computing device, a microcontroller with processor, voltage regulators, defibrillator charge and switch, power supply, capacitors, etc. The applicator body 210 also houses the microcontroller with main processor, voltage regulators, defibrillator charge and switch, power supply, capacitors, and other components of the overall device.

Returning to FIG. 2, In some versions, communication with external devices such as laptops, wireless networks, wearable electronic devices, smartwatches, servers, tablets, phones, etc., may be accomplished with wireless and wired communication 57 (e.g., via an antenna), in particular 802.11, Bluetooth, Zigbee, RS232 or other known wired or wireless communication protocols. The electronics (described in more detail below) are configured to control and provide electric shock treatment to the patient using the electrodes 260a, 260b via the defibrillation output 220a of the ACD Resuscitation device 200 and read an ECG signal measured by the electrodes 260a, 260b via the ECG input 220b of the ACD Resuscitation device. In some implementations, the electrodes 260a, 260b are removable from the ACD Resuscitation device 200. For example, the electrodes 260a, 260b can each be unplugged from the connection interface. For example, the rescuer might want to swap one of the electrodes 260a, 260b of the electrode assembly with another electrode. In some cases, the rescuer may want to use dedicated ECG electrodes and/or defibrillation electrodes, where the dedicated electrodes may provide more advanced capabilities than would otherwise be the case.

In some implementations, the electrodes 260a, 260b are packaged with the ACD Resuscitation device 200 such that they are stored proximate the applicator body 210 before being deployed for use. For example, the electrodes 260a, 260b can be latched to or stuck on a side of the applicator body 210 along fold lines 262a and 262b. For example, the electrodes 260a, 260b can be deployed with a compressed mechanical spring. When the electrodes 260a, 260b are needed, the rescuer can peel away a packaging holding the electrodes proximate the applicator body 210, press a button to release the electrodes, and so forth. Other storage configurations are conceivable. As shown in FIGS. 3B and 4C, electrodes 260c and 260d may be stored in a rolled format, so that they don't interfere with the therapeutic function of ACD compressions. Pull-tabs 261 may be provided to provide easy deployment of the self-adhesive electrodes onto the patient's chest when it is the appropriate time for defibrillation of the patient.

The ACD Resuscitation device includes a sensor package 230. The sensor package may include a compression sensor 240. The compression sensor may be a force sensor, a motion sensor, a tilt sensor, e.g. the ADXL345 (Analog Devices, Norwood, Mass.). In an embodiment, the force sensor may be a film-based, piezoresistive sensor such as the FlexiForce sensors, manufactured by Tekscan (Boston, Mass.)

For example, a computer processor 40 of the electronics can read data from one or more sensors (e.g., the compression sensor 240) of the ACD Resuscitation device 200, such as from the sensor package, or from one or more external devices. For example, the ACD device can include a port 235 for interfacing, either wirelessly or using a wired connection, with one or more remote devices, such as another AED, a smart phone, an external monitor, the central server, and so forth. Accordingly, the ACD Resuscitation device 200 may establish a wired or wireless connection with one or more remote devices and, for example, transfer data associated with the rescue event there between. For instance, the ACD Resuscitation device 200 may establish a connection with a tablet that is on scene, a remote computer at a hospital and/or a cloud server and transmit patient data collected by the device for review by other medical personnel. Such patient data may include, for example, ECG data of the patient, defibrillation shock information (e.g., energy level, number of shocks), CPR information (e.g., chest compression depth, chest compression rate, CPR pause, CPR idle time, ventilation information), drug administration history, and/or other relevant information. Once the connection is established, the ACD Resuscitation device 200 may also receive information from a separate device, such as instructions for the rescuer in providing more appropriate medical treatment than would otherwise be the case.

FIG. 3A illustrates a top view of the ACD Resuscitation device (e.g., active compression decompression ECG device 200 in FIG. 2). The ACD Resuscitation device 200 includes a rescuer end 265 having a handle 310, and an applicator body 370. The handle 310 of the rescuer end 265 includes two handgrips 310a, 310b and a graphical user interface 320. The ACD Resuscitation device 200 can be configured for being used to assist with multiple CPR and defibrillation treatments. The ACD Resuscitation device 200 can be switched on and turned off by pressing and holding down a power button (e.g., button 305) for a predetermined amount of time, for example five seconds. During this time, the graphical user interface 320 can display the battery life remaining in hours. If the power button is not held for a sufficient amount of time (e.g. five seconds) the ACD Resuscitation device 200 can remain on, and automatically power off after five minutes if no compressions or ECG signals are sensed.

The ACD Resuscitation device 200 can be configured to provide a predetermined number of hours of use. For example, the ACD Resuscitation device 200 can be designed to provide about 30 hours of use. At any time, a rescuer can determine the remaining battery life by pressing and holding a power button. The graphical user interface 320 can display the amount of time remaining, for example by displaying the letter H followed by a number. The number can indicate the number of hours of battery life remaining. In some implementations, the graphical user interface 320 can display an alert when the ACD Resuscitation device 200 has less than one hour of battery life remaining.

FIG. 3B illustrates a cross-sectional view showing the location of the various defibrillator components of the ACD Resuscitation device located within the handle 310 and applicator body 370. FIG. 10 shows a block diagram of the circuitry 1001 performing the defibrillation and monitoring functions. The monitoring and ECG circuitry 52 and defibrillation charging, storage and switching circuitry 10 either generate or are exposed to high voltages that might be lethal to the caregiver grasping the handles 310A and 310B. Optoisolators 58 as well as plastic insulating regions 53 are included to protect the caregiver from potentially lethal defibrillation voltages and currents.

In one embodiment, the defibrillation and energy storage function of the ACD Resuscitation device 200 is made up of at least a defibrillator charge and switch module 55 and one or more defibrillator energy storage capacitor(s) 56. In some embodiments, the more structurally rounded elements such as the defibrillator energy storage capacitor(s) 56 are housed in the rounded stem 280 while the more planar shaped, low-profile defibrillator charge and switch module 55 is housed in the planar shaped handle 270. Batteries 54, which are typically of a cylindrical shape, may also be housed in the more rounded areas of the handles 310A and 310B. In some implementations, the defibrillator circuitry of FIG. 10 is powered by a power supply 47. Other planar shaped elements like circuit boards or modules, e.g. monitor and ECG and power supply 47, main processor board 59, and display 320 can also be housed in the handle 270. Vertical structural reinforcing elements 311, fabricated from lightweight, rigid materials such as carbon fiber, aluminum, or fiberglass may be added to the internal sides of the handle 270 to withstand downward forces on the handles 310a and 310b that may exceed 100 pounds during chest compressions. It can be appreciated that other arrangements are possible.

Turning to FIG. 10, the circuitry 1001 includes one or more of real-time clock 44, a system clock 43, a reset circuit 48, an analog to digital converter 45, a digital to analog converter 46, input keys 51, read-only memory 41, random access memory 42, and general purpose inputs/outputs 49. These elements are described in greater detail with respect to FIG. 11.

Returning to FIG. 3B, the handle 310 of the rescuer end 265 is attached to the applicator body 370. The applicator body 370 can be releasably attached to a coupling surface 390 using a coupling mechanism (e.g., coupling mechanism 330 of FIG. 3B). In some implementations, the applicator body 370 can be attached to the coupling surface 390 via a magnet. In some implementations, the magnetic coupling is configured such that applicator body 370 becomes detached from coupling surface 390 when excessive decompression force (upward pull) is applied. Other means to couple the applicator body 370 to the coupling surface 390 include various mechanical connections including ball and socket, cantilevered arm, or detent mechanism or the like.

FIG. 3B illustrates an example of a magnetic coupling mechanism in an external chest compression and decompression system. FIG. 3B provides a cross-section view of compression and decompression the ACD Resuscitation device 200, which includes the applicator body 370 releasably coupled to the coupling surface 390, which is attached to an adhesive pad 395. The ACD Resuscitation device 200 can include a coupling mechanism 330 between the coupling surface 390 and the applicator body 370.

The coupling mechanism 330 includes a magnet assembly disposed on or coupled with the applicator body 370, and a keeper assembly disposed on or coupled with the coupling surface 390. In some implementations, the coupling mechanism 330 can include the magnet 340, or magnet assembly, and keeper assembly 350. The magnet 340 or magnet assembly can be coupled with (or part of) the applicator body 370. The keeper assembly 350 can be coupled with or part of the coupling surface 390. The magnet assembly and keeper assembly 350 in combination can be referred to as a coupler assembly. In some implementations, the magnet 340 can include or be part of a magnet assembly having a magnet, a non-ferrous spacer, and a ferrous container for directing the magnetic flux from the pole of the magnet furthest away from the magnet keeper to the magnet keeper assembly 350. The poles of the magnet can be arranged such that the poles are aligned along the axis 380 of the system piston. The magnetic keeper on the coupling surface 390 of the ACD Resuscitation device 200 can include a magnet with poles arranged in the opposite direction of the system handle magnet or of a ferrous material such as 12L14 carbon steel having a high capacity for carrying magnetic flux. A magnetic coupling between the applicator body 370 and the coupling surface 390 can be effortless. In some implementations, the force of the disconnection of the magnetic coupling can be stable over a wide range of operating environments.

In some implementations, the coupler assembly can operate to provide a consistent release force allowing the applicator body 370 to separate from the coupling surface 390 prior to the adhesive pad 395 releasing from the patient' skin. In addition, it may be desirable that the magnet assembly does not have a magnetic field that is widely dispersed, but rather focused in the direction of the keeper. To focus the magnetic field, the magnet assembly can include a magnetic core, a non-magnetic sleeve, and a ferromagnetic pot which conducts the magnetic flux from the pole on the enclosed side of the magnet to the open side of the magnet. The arrangement of a jacket with the magnet can focus the majority of the magnetic flux to the open end of the assembly. For example, a magnet assembly of coupling mechanism 330 may include a magnetic core 340, a non-magnetic sleeve, and a ferromagnetic pot, which conducts the magnetic flux from the pole on the enclosed side of the magnet 340 to the open side of the magnet 340. The arrangement of a jacket with the magnet can focus the majority of the magnetic flux to the open end of the assembly 360. Control or selection of the material properties of the keeper 350 can be helpful to achieve a consistent release force. In some implementations, the material can have a high magnetic saturation such as a 12L14 or American Iron and Steel Institute (AISI) 1010 or 1020 material and the magnetic properties of the material can be controlled through the control of material temper. For example, materials can be processed to a fully annealed condition. In addition to the magnetic coupling mechanism described herein, other types of breakaway mechanisms can be used in an external chest compression and decompression for coupling the coupling surface 390 with the ACD Resuscitation device 200. Examples of breakaway mechanisms can be configured to allow the ACD Resuscitation device 200 to disengage from the coupling surface 390 in a controlled manner.

Figure 3D:
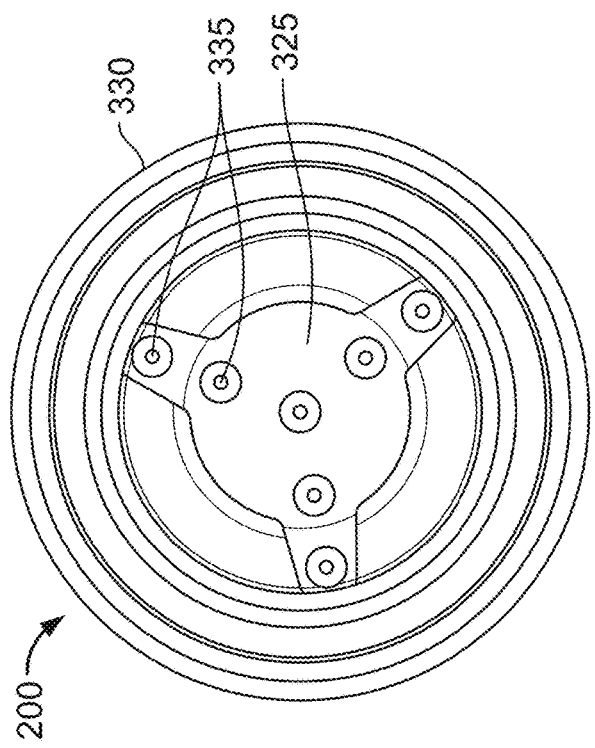
FIGS. 3C-3E show bottom views of an example ACD Resuscitation device.
Figure 3C:
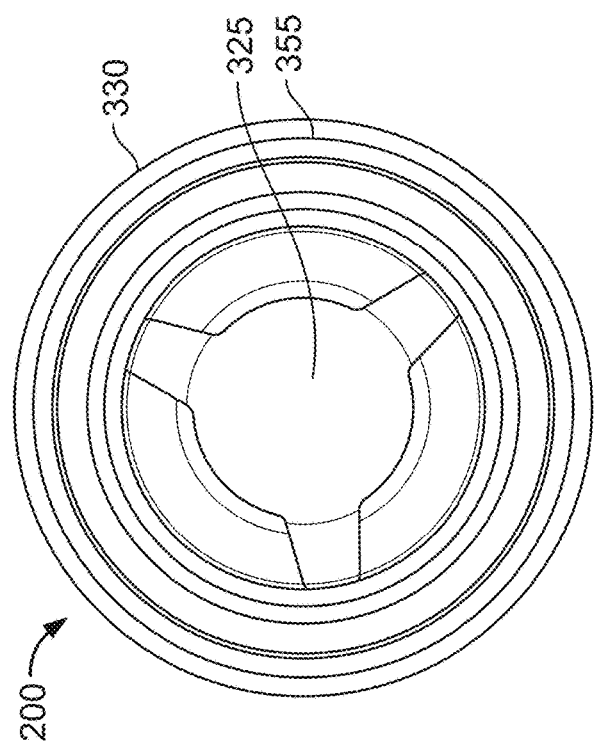
Figure 3E:
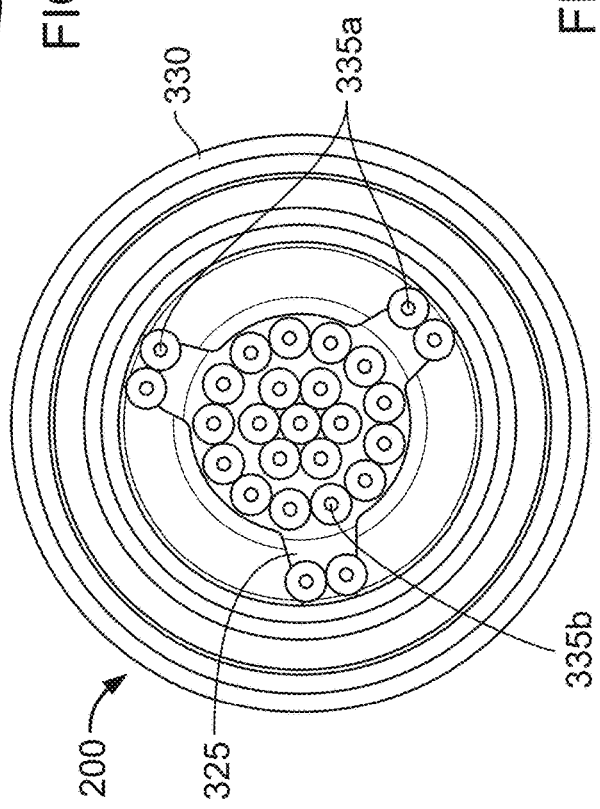

FIGS. 3C-3E illustrate examples of bottom views of a coupling mechanism 335 of the ACD Resuscitation device 200. The bottom views include the coupling mechanism 335 of the ACD Resuscitation device 200 (e.g., applicator body 210 of the ACD Resuscitation device 200 described with reference to FIG. 2). In some implementations, the coupling mechanism 335 can be a plunger. The coupling mechanism 335 includes a distal end (not shown) and a proximal end 355. The proximal end 355 defines the part of the coupling mechanism 335 that extends from the coupling mechanism 335. The distal end 345 defines the part of the coupling mechanism 335 that impacts the patient's chest through the coupling surface 390. The coupling mechanism 335 can include one or more check valves allowing fluid to escape the passageway during attachment to the coupling surface (e.g., coupling surface of FIGS. 3A-3B), but preventing fluid from entering the passageway via the check valves. The check valves include one or more of duckbill valves, umbrella valves, cross slit valves, ball-check valves, cone-check valves, and swing valves.

In some implementations, the coupling mechanism 335 includes a compression pad 325. The compression pad can be a flexible surface element configured to regulate the force applied to the patient's chest through the air passageway of the coupling surface. The compression pad 325 can include an adhesive layer. The compression pad 325 can include one or more suction cups 335 that apply compression and decompression forces to the patient's chest, such as through the coupling surface 390. The adhesive layer can line the margins of the suction cups 335. The compression pad 325 can be secured to the coupling surface 390 by suction created by the suction cups 335 formed on distal end 345. A rescuer can pull back the ACD Resuscitation device 200, which in response extends the coupling mechanism 335, to confirm secure coupling between the compression pad 325 and the coupling surface 390.

The compression pad 325 can include a stiffness that increases from margins towards a geometrical center of the compression pad 325. The compression pad 325 can present any suitable complex shape, including multiple appendages, arms or lobes. Each arm or lobe of the compression pad 325 can contain numerous suction cups 335. The use of multiple lobes enables the compression pad 325 with many suction cups 335 to conform to irregularities in the top layer of the coupling surface 390 (e.g., irregularities due to sensor and wire inclusions). The lobes of the compression pad can be conformable and inelastic to convey the decompression force between ACD Resuscitation device 200 and the coupling surface 390.

In some implementations, the size and/or shape of the suction cups 335 can be selected based on one or more characteristics of the coupling surface 390. In some implementations, the number and the location of the suction cups 335 can be selected based on one or more characteristics of the coupling surface 390. For example, the suction cups 335 can be arranged in two groups 335a and 335b, distanced from each other, such that no suction cup covers the passageway of the coupling surface 390 during coupling between the compression pad 325 and the coupling surface 390.

Figure 4A:
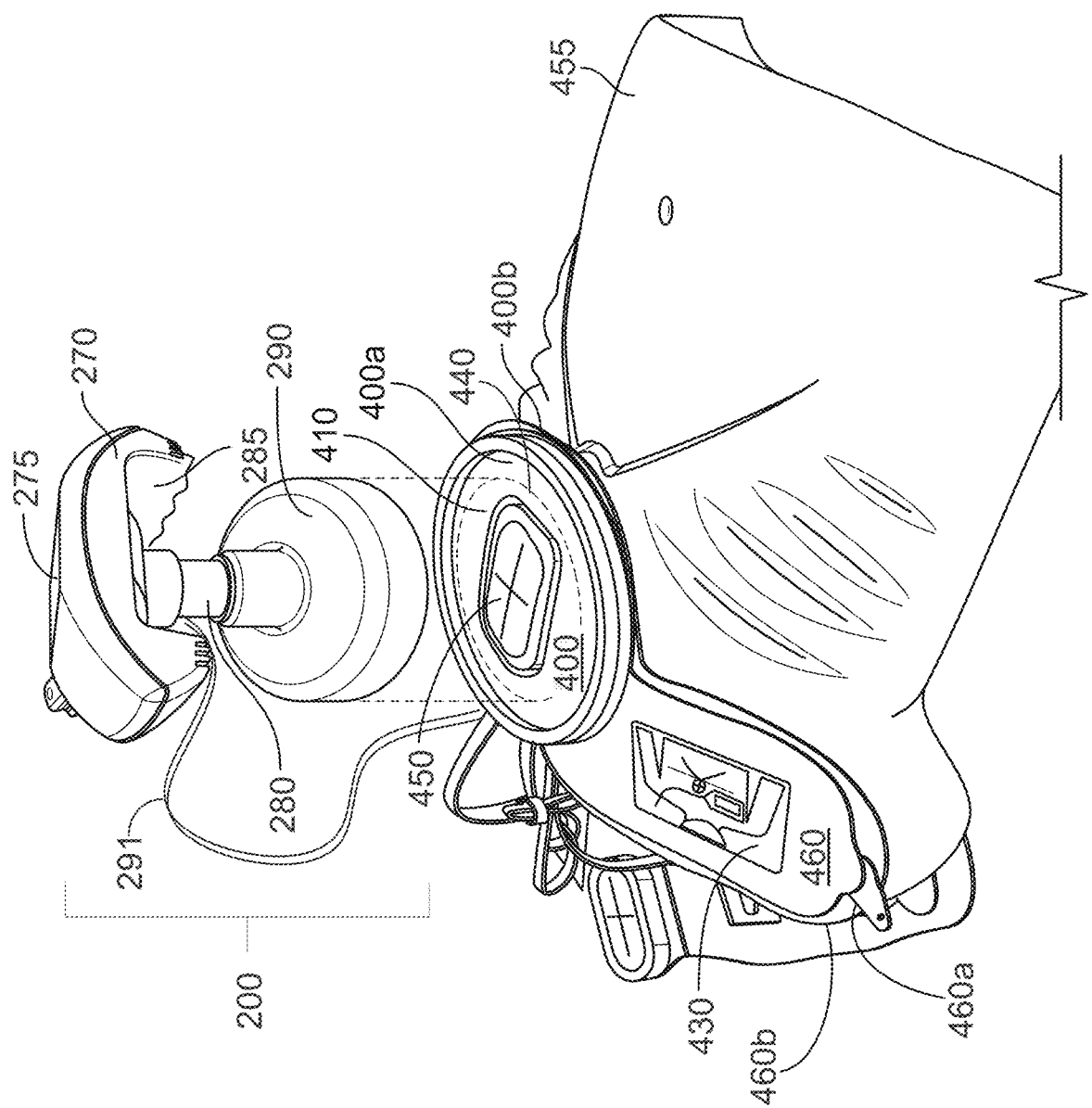
Figure 4C:
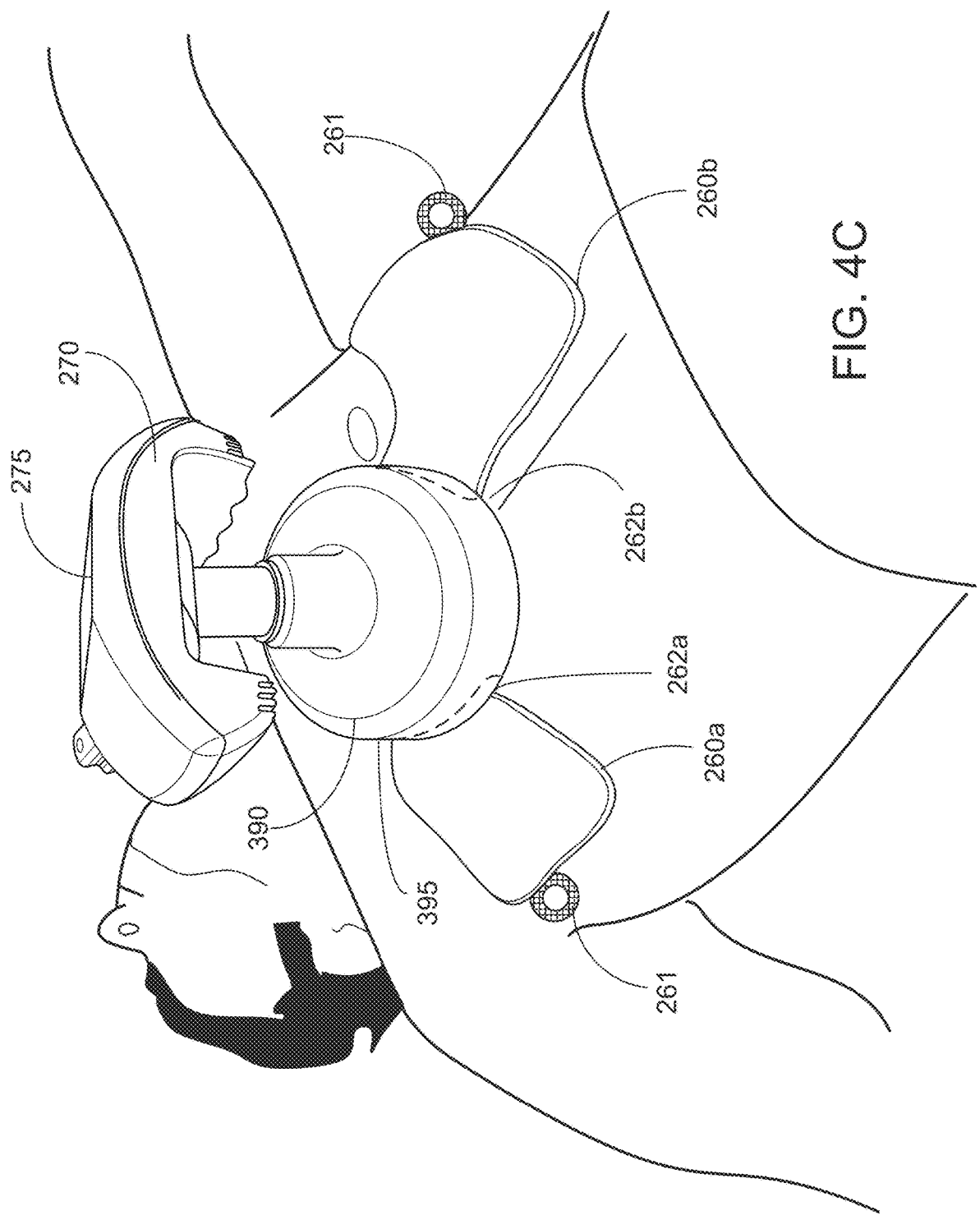

Turning to FIG. 4A, a coupling platform 400 can include a landing pad 410 for the coupling mechanism 290 of the ACD Resuscitation device 200. In some implementations, the landing pad 410 includes a surface that complements, for example, as size and geometry, the coupling mechanism 290. In some implementations, the coupling platform 400 includes a compliant and resilient material, such as a natural or synthetic foam. In some implementations, the coupling platform 400 includes an attachment member (not shown) complementary to a corresponding attachment member (not shown) of the ACD Resuscitation device 200. Each of the mechanical attachment members 218a and 218b can include a mating interface. The attachment members and can include mechanical gearing, hydraulics, pneumatics, and/or electromagnetic coupling. For example, the attachment members and can form a pneumatic system for increasing or enhancing a vacuum between the coupling mechanism 290 and the coupling platform 400. The attachment members and can also be configured to act as actuators to release the vacuum holds of the attached coupling mechanism 290 from the coupling platform 400, for instance, by injecting air into the coupling mechanism 290. The attachment members and can include well-known components such as a pump, valves, and/or fluid transfer lines.

In some versions, the electrical connection between the defibrillator charge and switch module 55 and the electrodes 260a and 260b may be accomplished with a cable 291 coupled through a complementary high voltage connector 220a capable of withstanding voltage discharges commonly associated with defibrillation shocks, as understood by those of skill in the art. Alternatively, high voltage wiring may be routed through the applicator body 370 to a corresponding high voltage connector 220b located at the base of applicator body 370 that mates with high voltage connector 220c located on the coupling surface 390. With this second version, the electrical connection is established between the ACD Resuscitation device 200 and the electrodes 260a and 260b as soon as the applicator body 370 is mated with the coupling surface 390.

In some implementations, the ACD Resuscitation device 200 includes a passageway 440 (marked by a dashed line) located between a compression sensor 450 and the coupling platform 400. The passageway 440 can be configured to optimize the propagation of the compression and decompression forces from the ACD Resuscitation device 200 to the patient's chest. The dimensions of the passageway 440 can be chosen relative to the base of coupling mechanism 290 and the surface of the compression sensor 450. For example, the passageway 440 can substantially encircle the compression sensor 450, such that the inner diameter of the passageway 440 is at least equal or larger than the outer diameter of the compression sensor 450. The passageway 440 can be completely encircled by the base of the applicator body 218, such that the outer diameter of the passageway 440 is at least equal or smaller than the inner diameter of the base of the coupling mechanism 290. The passageway 440 can have multiple configurations and structures.

An adhesive pad 460 can include an alignment feature 430. The alignment feature 430 can be included in the upward facing portion of the adhesive pad 460. The alignment feature 430 can guide a rescuer in attaching the adhesive pad 460 to an optimal portion of the patient's chest, such as using text or pictorial instructions. The adhesive pad 460 can include a liner 460a and an adhesive face 460b. The liner 460a can be removed or peeled away from adhesive face 460b by a rescuer for attaching the adhesive pad 460 to the patient body 455. The adhesive face 460b can be configured to be releasably attached to the patient's chest, for example on the sternum at the mid-nipple line as shown in FIGS. 2A-2D.

The adhesive face 460b can include a layer of high-traction or anti-slip material for contacting the skin of the patient body 455, such that the adhesive pad 460 remains attached to the patient's skin during CPR treatment. In some implementations, the adhesive face 460b can include pressure-sensitive adhesives, such as medical bandage adhesives, transdermal patches, and other medical applications. In some implementations, the adhesive face 460b can include natural and synthetic rubber-based formulations, such as polyisobutylenes, and acrylic and silicon-based materials, and swollen hydrogels, such as polyvinyl pyrrolidone, which are suitable in conjunction with electrodes. At completion of a CPR treatment or defibrillation with the integrated treatment system 100, the adhesive face 460b can be removed by conventional means, e.g., by applying a solvent to the adhesive and/or peeling the adhesive face 460b away from the patient's chest.

The dimensions of adhesive pad 460 can be chosen to provide a desired contact area with the patient's chest. In some implementations, the larger the surface of the adhesive pad 460, the more expansion of chest can be achieved using an integrated treatment system 100 (e.g., if the patient's chest is compliant or if a rib has been broken). Typically, for adult patients, adhesive pad 460 can have a generally square or rectangular shape. For children, the dimensions can be smaller. Other shapes can also be useful. For example, it can be desirable to shape the lower surface 400b of the adhesive pad 460 to conform to the general contours of the patient's chest. In addition, it may be desirable to provide a plurality of sizes and shapes of adhesive pads in a single kit so that an adhesive pad can be selected for the individual patient. The thickness of the adhesive pad 460 can depend on the resiliency of the material employed. For manual CPR operation, the adhesive pad 460 can be about 10 cm by 40 cm.

The adhesive pad 460 can include an electrode (e.g., one or both of electrodes 260a, 260b) configured to transmit a defibrillation current to the patient body 455 as well as simultaneously monitor the ECG of the patient. The adhesive pad 460 can include or be coupled to the compression sensor 450. The compression sensor 450 can be configured to measure at least one chest compression parameter during CPR treatment. A wire can provide an electrical connection between the compression sensor 450 and the ACD Resuscitation device 200. In some cases, the signals detected by the compression sensor 450 are used to initiate and optimize the CPR treatment. Examples of electrode and sensor configurations are further described with reference to FIGS. 5A and 5B.

In some implementations, the coupling platform 400 at least partially surrounds the compression sensor 450 and/or at least a portion of the wire. The coupling platform 400 can be an integrated part of the adhesive pad 460 or it can be releasably attached to the adhesive pad 460. The coupling platform 400 includes the upward facing portion 400a and the downward facing portion 400b. The downward facing portion 400b can be configured to maintain adherence with the adhesive pad 460. The upward facing portion 400a can be configured to maintain adherence with the ACD Resuscitation device 200. The adherence between the coupling platform 400 and the ACD Resuscitation device 200 can be sufficient to transfer a decompression force between the ACD Resuscitation device 200 and the patient's chest during the CPR treatment or defibrillation without detaching. The upward facing portion 400a can be substantially smooth.

FIG. 4B illustrates a perspective view of a portion of the integrated treatment system 100, in which ACD Resuscitation device 200 is attached to the coupling platform 400. The illustrated arrangement of the ACD Resuscitation device 200 can be used by a rescuer for performing both active compressions and decompressions for manual CPR treatment and for measuring ECG signals and performing defibrillation. The configuration of the ACD Resuscitation device 200 enables the rescuer to press down on the upper surface 275 of handle 270 with the palms of the hands to apply a compressive force against coupling platform 400 and patient's chest over a compressive/decompressive area, such as adhesive pad 460. The configuration of the ACD Resuscitation device also allows the operator to lift up by pressing on the lower surface 285 of the handle 270 with the fingers. Since lower surface 460b of the adhesive pad 460 is adhered to contact area of patient's chest, the lifting motion on handle 270 lifts and expands patient's chest.

Referring to FIG. 5A, an example of an integrated treatment system 500 is shown. In this example, the ACD Resuscitation device 200, is separate from the electrodes 260a and 260b and the electrodes 260a and 260b are electrically connected via cable 291. The cable 291 can include a number of wire leads that are connected together by a common plastic shroud that can surround the wires or can have been integrally formed around the wires such as through an extrusion process, and can be connected by way of a connector 220a. The wires can carry power from the defibrillator charge and switch module circuitry 55, such as current to provide a shock to a patient who is being provided with emergency care, and/or to the monitor and ECG and power supply circuitry 47, such as in the form of signals for generating ECG data, accelerometer data, and measurements of trans-thoracic impedance of a patient.

The electrode assembly in this example includes a first electrode 540, a second electrode 550, and a chest compression assembly 560. In some implementations, the first electrode 540 can be configured to be placed above the patient's right breast, while the second electrode 550 can be configured to be placed below the patient's left breast. During a rescue operation, printed insignia on one or both of the electrodes 540, 550 can indicate to a rescuer how to deploy the electrodes 540, 550, and where each of them should be placed. In addition, the defibrillator 510 can display such instructions on a graphical display (such as user interface 610 described in reference to FIG. 3A) and can also provide verbal instructions to supplement was is shown in the visual instructions, such as instructions for the sequential operation of the defibrillator 510. In some implementations, the electrodes 540, 550 can be electrodes 260a, 260b of FIG. 2.

In some implementations, the electrode assembly 520 includes a sensor packet, such as a chest compression assembly 555. The chest compression assembly 555, in this example, includes a detector housing 570 a display 580, e.g., through ACD Resuscitation device 200. The detector housing 570 can include a plastic housing within which is mounted an assembly containing a compression sensor 240. The compression sensor 240 may be an accelerometer. The accelerator assembly can move with the housing as chest compressions and decompressions are performed on a patient so that motion of the accelerometer matches motion of the patient's sternum. The detector housing 570 is shown in the figure as having an "X" printed on its top surface to indicate to the rescuer where to place his or her hands when delivering chest compressions and decompressions to a patient. The accelerometer in the housing can be connected to pass signals through cable 291 to connector 220a. The compression sensor or sensors may be configured to be electrically isolated from the electrodes 260a 260b, in which case, the compression sensor signals can be connected directly to the A/D conversion circuitry 45 via electrical pathways. Alternatively, the compression sensing may connect to the Monitoring and ECG Signal Acquisition and Processing circuitry 52 via an electrical pathway. Digitized signals are then processed for estimating conditions about the rate and depth and other measures of quality of compressions and decompressions being performed on the patient. In some implementations, the ACD Resuscitation device 200 can be affixed to the applicator body 210 along with the electrodes 260a, 260b and deployed for use along with the electrodes 260a, 260b, or configured as shown in FIG. 3B or 4C.

The display 580 provides feedback that is directed to the rescuer who is performing chest compressions and decompressions. In some implementations, the display 580 can be a part of the user interface (e.g., user interface 610 of FIG. 3A). In this example, the feedback comprises symbols similar to those shown on the user interface 610 of the ACD Resuscitation device 200, in particular, a real-time representation of the rescuer who performs chest compressions and decompressions synchronously displayed with an optimized rescuer position. The representation can be selected to be independent of the orientation from which it is viewed, so that it has the same meaning to a rescuer who is on the right side of the patient as to a rescuer who is on the left side of the patient. In that manner, the integrated treatment system 500 does not need to determine where the rescuer is positioned relative to the display. Also, a haptic vibrating mechanism can be provided at the assembly 560, so as to provide tactile beats or metronomes for a user to follow in providing chest compressions and decompressions using the ACD Resuscitation device 200.

FIG. 5B shows a slightly different arrangement. The electrode 545 can simply be a single electrode that is connected to receive energy from the defibrillator, and is arranged to be placed in a conventional manner above a patient's right breast. The electrode 545 can also include mechanisms for sensing an ECG reading from a patient, and for communicating sensed parameters back to the defibrillator 510.

The assembly 555 can present a slightly L-shaped form, with one leg comprising an electrode designed to be placed below a patient's left breast, and another leg arranged to lie in a line with the patient's sternum. The assembly 555 can be mounted on a flexible foam later that includes a gel layer on the bottom of the electrode for conducting a shocking pulse to a patient, but no gel under the sensor portion. However, the sensor portion can have a form of adhesive on its bottom side so that the accelerometer does not bounce and separate from the patient during chest compressions and decompressions, and thus give an inaccurate reading to the ACD Resuscitation device 200.

In this example, the hypothetical patient is shown in dotted lines to indicate how the electrode 545 and the assembly 555 can be positioned in actual use. Before they are deployed, however, the various electrodes and assemblies can be stored in a sealed packet, and the wires can be coiled to reduce needed space, in conventional manners. At the time of an emergency, the wires can have already been plugged into the connector 220a of the ACD Resuscitation device 200 (e.g., via the wires extending through a sealed hole out of a packet in which the electrodes are stored to keep their gels moist). A rescuer can then open the package, plug the wires in if they are not already plugged in, and if necessary, read instructions on the back sides of the electrodes regarding the proper manner to apply the electrodes (e.g., with graphics that show the peeling off of covers over the electrode gels and also show images of the proper placement of the electrodes on a line-drawn patient). In some implementations, the electrodes 540, 550 may be configured to deploy a conducting gel onto the patient when the electrodes 540, 550 are affixed to the patient. For example, the conducting gel may be released upon the application of a sufficient amount of pressure to the electrodes, or a user may release the conducting gel from a storage reservoir (e.g., opening of a sealed package, releasing a valve or passageway that allows the conducting gel to flow).

In addition to one or more electrodes, the assembly 555 can include the detector housing 570 and the display 580. In some implementations, the housing 570 is connected directly to the electrode 555 by a flexible structure that is arranged and sized so as to place the electrode and sensors in appropriate locations for a patient (under a left breast and aligned over the top of the sternum). In some implementations, the assembly is a part of the coupling mechanism of the ACD Resuscitation device 200 (e.g., coupling mechanism 290). Such an arrangement allows the integrated treatment system 590 to have fewer components that need to be applied to a patient than the integrated treatment system 500, while still having the flexibility to space the two electrodes relative to each other depending on the size of the patient (e.g., because the electrodes are separate from each other, it can be easier to position them both on small patients and very tall/long patients).

Feedback devices away from the main medical device can also take other forms. For example, a top surface of one of the electrodes or near a puck can include an LED (not shown). In some implementations, the LED can blink to indicate a rate of chest compressions and decompressions to be performed. In some implementations, the LED can stay solid on to indicate that rescuers should switch positions. In some implementations, an LED or graphical display can be provided on the ventilation bag. In some implementations, the ventilation bag LED blinks to indicate a rate at which the bag is to be squeezed. In some implementations, the ventilation bag LED is solid in coordination with a signal from the display 580 for the person performing chest compressions and decompressions. For example, the LED signals are coordinated on different components of the integrated treatment system 500, 590. As a result, the rescuers will only need to know a single "change" signal and will be able to react more intuitively and more quickly.

As illustrated in FIG. 3A, an ACD Resuscitation device 600 includes a user interface 610. The user interface 610 provides controls, such as controls 620, for operating the ACD Resuscitation device 600. A display 630 of the user interface 610 is configured to provide real-time feedback to the rescuer for active compression and decompression CPR treatment and for defibrillation treatment. For illustrative purposes, two particular examples of feedback are shown on a display 630 of ACD Resuscitation device 600 (e.g., ACD Resuscitation device 200 described with reference to FIG. 2). For example, as shown on display 630, during the administration of chest compressions and decompressions, the ACD Resuscitation device 600 displays data about the chest compressions and decompressions in box 640, such as compression depth, rate, elapsed time, and so forth. For example, the display 630 shows a filtered ECG waveform 650 and a $CO_2$ waveform 660 (alternatively, an $SpO_2$ waveform can be displayed).

In some implementations, the ACD Resuscitation device 600 is configured to generate the ECG waveform 650 during chest compressions and decompressions by the rescuer. The ACD Resuscitation device 600 generates the ECG waveform 650 by gathering ECG data points and accelerometer readings, and filtering the motion-induced (e.g., CPR-induced) noise out of the ECG signal received from the electrodes (e.g., electrodes 260a, 260b of FIG. 2).

Measurement of velocity or acceleration of chest compression during chest compressions can be performed according to the techniques taught by U.S. Pat. No. 7,440,335, titled Method and Apparatus for Enhancement of Chest Compressions during Chest Compressions, the contents of which are hereby incorporated by reference in their entirety. Displaying the filtered ECG waveform 650 helps a rescuer reduce interruptions in CPR because the displayed waveform is easier for the rescuer to decipher. If the ECG waveform 650 is not filtered, artifacts from manual chest compressions and decompressions can make it difficult to discern the presence of an organized heart rhythm unless compressions and decompressions are halted. Filtering out these artifacts can allow rescuers to view the underlying rhythm without stopping chest compressions and decompressions.

In some implementations, the ACD Resuscitation device 600 synchronizes active compression and decompression CPR treatment and defibrillation of the patient. For instance, the defibrillator may be timed to shock at a particular phase of the chest compression cycle, as described in U.S. Pat. No. 8,478,401, entitled "Synchronization of defibrillation and chest compressions," the contents of which are hereby incorporated by reference in their entirety. The timing of the defibrillation shock may be timed to correspond to a particular phase of either force exerted by the coupling mechanism 290 on the patient's sternum, or the estimated motion of the patient's sternum. The force sensor and/or motion sensor 240a or 240b may be located in close proximity to the coupling mechanism and the patient's sternum to get a more accurate measure of the forces exerted upon and localized motion of the patient's sternum. The timing of the defibrillation may also incorporate analysis of the ECG waveform, for instance as described in WO2016154425, entitled "Amplitude Spectrum Area Considerations for an External Medical Monitoring and Treatment Device," the contents of which are hereby incorporated by reference in their entirety, or analysis of other physiological signals such as $SpO_2$ or impedance cardiography or impedance pneumography.

In some implementations, the CPR data in box 640 is automatically displayed when compressions and decompressions are detected by the ACD Resuscitation device 600. For example, the data about the chest compressions and decompressions that is displayed in box 640 includes rate 670 (e.g., number of compressions and decompressions per minute). For example, the data about the chest compressions and decompressions that is displayed in box 640 includes and depth 680 (e.g., depth of compressions and decompressions in inches or millimeters). In some implementations, the display 630 shows other CPR data in the box 640, such as elapsed time of treatment (in seconds and minutes), instructions (push harder, push softer, increase rate, decrease rate, etc.), and so forth. In some implementations, the ACD Resuscitation device 600 determines the rate 670 and depth 680 of compressions and decompressions by analyzing accelerometer readings, such as measured using one or more accelerometers of a sensor package attached to the ACD Resuscitation device 600. By displaying the actual rate 670 and depth 680 data, such as in addition to, or instead of, an indication of whether the values are within or outside of an acceptable range, the ACD Resuscitation device 600 provides useful feedback to the rescue, such as during treatment of the patient by the rescuer. For example, if an acceptable range for chest compression depth is 25 to 60 mm, providing the rescuer with an indication that his/her compressions and decompressions are only 15 mm enables the rescuer to determine how to correctly modify administration of the chest compressions and decompressions.

In some implementations, the CPR data in box 640 includes a perfusion performance indicator (PPI) 690. In some implementations, the PPI 690 is a shape (e.g., a diamond) including an amount of fill that is in the shape. The fill differs over time to provide feedback about both the rate and depth of the compressions and decompressions in a graphic form. For example, when CPR is being performed adequately, such as at a rate of about 100 compressions and decompressions per minute (CPM) with the depth of each compression greater than 40 mm, the entire indicator is filled. For example, as the measured rate and/or depth decreases below acceptable limits, the amount of fill of the shape lessens. The PPI 690 provides a visual indication of the quality of the CPR such that the rescuer can aim to keep the PPI 690 completely filled. Such a graphic reference is intuitive to untrained rescuers and is readable at a glance during treatment. For example, the PPI 690 may be easier to read and understand by a rescuer when the display 630 of the ACD Resuscitation device 600 is moving during compressions and decompressions being performed by comparison to numerical readouts, which may be more difficult to read.

The ACD Resuscitation device 600 can use several different configurations for displaying treatment data to the rescuer. For example, as shown in the display 630, the filtered ECG waveform 650 is a full-length waveform that approximately spans the length of the display 630, while a second waveform (e.g., the $CO_2$ waveform 660) is a partial-length waveform and fills only a portion of the length of the display 630. In this example, a portion of the display beside the second waveform provides the CPR data in the box 640. In some implementations, the display 630 splits the horizontal area for the second waveform in half, displaying the $CO_2$ waveform 660 on the left, and CPR data on the right in the box 640. Other such configurations of the waveforms 650, 660, and box 640 are possible.

The ACD Resuscitation device 600 can change what data is presented on the display 630 based on the actions of the rescuer. For example, the CPR data displayed can change based on whether the rescuer is currently administering CPR chest compressions and decompressions to the patient. Additionally, the ECG data displayed to the user can change based on the detection of CPR chest compressions and decompressions. For example, an adaptive filter can automatically turn ON or OFF based on detection of whether CPR is currently being performed. When the filter is on (during chest compressions and decompressions), the filtered ECG waveform 650 is displayed and when the filter is off (during periods when chest compressions and decompressions are not being administered), unfiltered ECG data is displayed. An indication of whether the filtered or unfiltered ECG data is displayed can be included with the waveform. In some implementations, an indication of the filter parameters can be displayed or stored in association with the ECG waveform data. For example, if the filtered ECG data are sent to a data processor (either local or remote) for subsequent data processing, the data processor can take the filtering parameters into account if necessary, such as for statistical or categorization purposes of the treatment records. In some implementations, the ACD Resuscitation device 600 can detect whether the device is upright (e.g., via an accelerometer). When the ACD Resuscitation device 600 is upright, the one or more processors of the ACD Resuscitation device 600 can determine that the device is being held by a rescuer and adjust instructions of the user interface in response. For example, the user interface can provide instructions for placement of the ACD resuscitation device 600 on the patient, or placement of electrodes, a coupling surface, or other sensors or devices on the patient.

In some implementations, a reminder 695 is included on the display 630. The reminder 695 is regarding "release" in performing chest compression. Specifically, a fatigued rescuer can begin leaning forward on the chest of a patient and not release pressure on the sternum of the patient at the top of each compression. This can reduce the perfusion and circulation accomplished by the chest compressions and decompressions. The reminder 695 can be displayed when the system recognizes that release is not being achieved (e.g., signals from an accelerometer show an "end" to the compression cycle that is flat and thus indicates that the rescuer is pressing on the sternum to an unnecessary degree). Such a reminder 695 can be coordinated with other feedback, and can be presented in an appropriate manner to get the rescuer's attention.

In some implementations, the visual indication is accompanied by a spoken or tonal audible feedback, including a sound that differs sufficiently from other audible feedback so that the rescuer will understand that release (or more specifically, lack of release) is the target of the feedback. For example, the ACD Resuscitation device 600 can emit a sound through a speaker 615, such as audible instructions ("release," "fully decompress," etc.). In some implementations, the sound is in the form of a metronome to guide the rescuer in the proper rate of applying CPR treatment.

Figure 6:
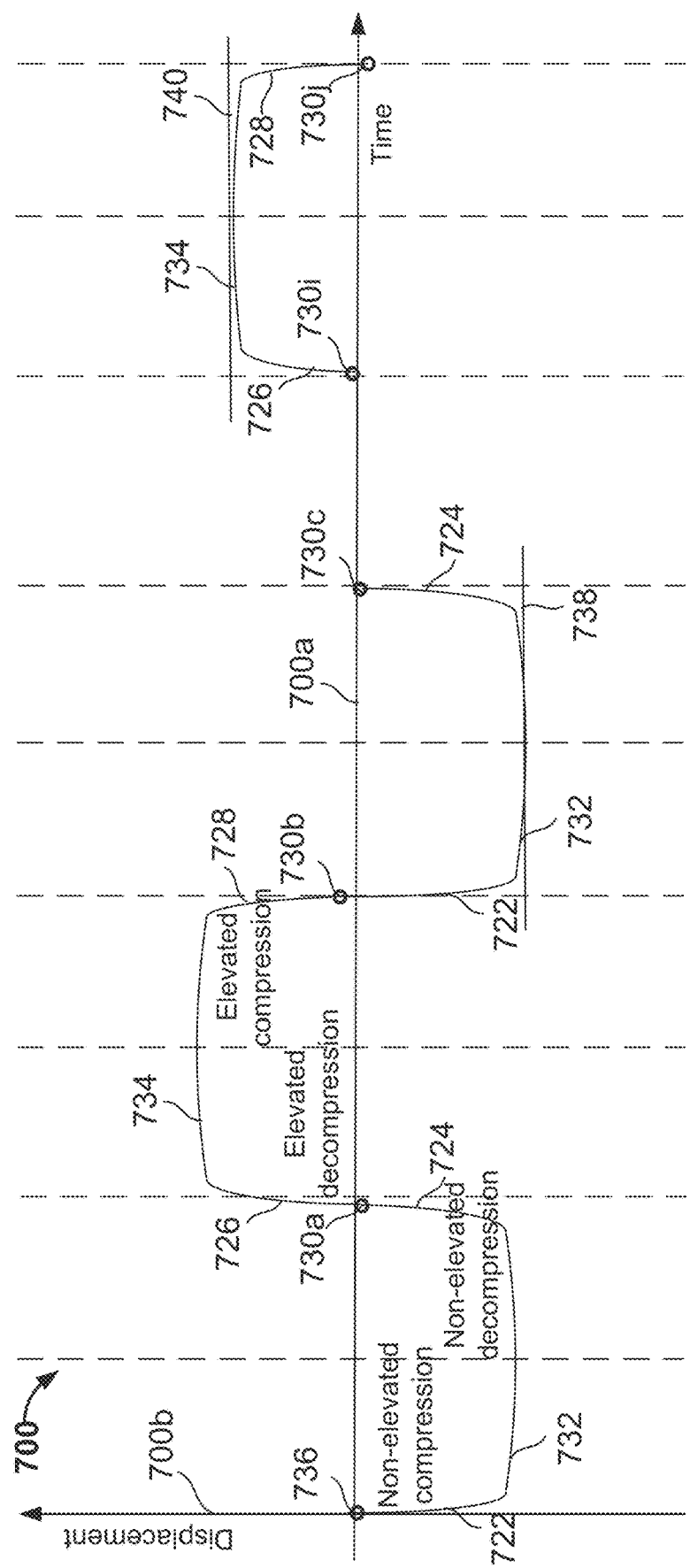
FIG. 6 shows a graph showing displacement vs. time of an example ACD CPR treatment.

FIG. 6 shows an example graph 700 including temporal variation of an example of a signal indicative of ACD CPR chest compression treatment, such as with ACD Resuscitation device 200. Here, the graph 700 illustrates an estimated displacement of the sternum on which ACD treatment is applied over time. In some implementations, graph 700 can be shown on a display associated with the ACD Resuscitation device 200, such as display 630 of FIG. 3B or on an external display.

The graph 700 illustrates transitions between one or more of the phases of the ACD CPR chest compression treatment, such as a compression phase 722, a non-elevated decompression phase 724 and an elevated compression phase 728 and the plateau phases 732 and 734, as could be performed through real-time feedback controlled treatment. The example graph 700 includes a temporal axis 700a and a displacement axis 700b, the intersection of which marks the neutral point 736 of the patient's chest. The transition points 730a-730j define the transitions between elevated and non-elevated phases of the ACD CPR chest compression treatment. In some implementations, some transition points (e.g., transition point 730c) can correspond to the neutral point 736 of the patient's chest wall (e.g., the level at which the chest wall would be if ACD CPR chest compression treatment would not be applied, which can be measured before the initiation of the ACD CPR chest compression treatment). Some transition points (e.g., transition points 730a, 730b, 730i, and 730j) can be above or below the neutral points 736 of the patient's chest wall.

In some implementations, the example graph 700 includes one or more plateau phases, such as a non-elevated plateau phase 732 and an elevated plateau phase 734. The plateau phases can correspond to a time of approximately constant compression and decompression force, respectively. The approximately constant force time can be included in the ACD CPR chest compression treatment to improve vascularization and oxygenation. The transition from a non-elevated compression or elevated decompression to a plateau phase can be a smooth transition, such that the variation of the compression or decompression force and/or displacement relative to time is gradually decreasing until the force or displacement remains approximately constant over a preset time. The preset time can be selected based on one or more physiological parameters. The preset time of a non-elevated plateau phase 732 can be sufficient to promote net blood flow to the head of the patient. The preset time of an elevated plateau phase 734 can be sufficient to promote net blood flow to the heart of the patient. The preset time corresponding to the non-elevated plateau phase 732 and/or the elevated plateau phase 734 can be between about 50-200 milliseconds.

In some implementations, the rescuer is guided into performing a smooth transition from an active compression or decompression to a plateau phase (e.g., corresponding to an exponential variation in the applied force until it reaches a particular compression threshold 738 and/or depression threshold 740). The compression threshold 738 and/or decompression threshold 740 can be selected based on physiological characteristics of the patient and/or ACD CPR chest compression requirements.

For example, the feedback provided to limit the decompression force above the neutral point below the depression threshold 740 can be configured to decrease the risk of rib fracture in a patient with a particular body structure. In some embodiments, the elevated decompression phase 726 and the elevated plateau phase 734 can be synchronized with patient's ventilation. Alternatively, the patient's ventilation can be synchronized to occur during both the non-elevated decompression and elevated decompression phases (i.e. substantially the whole of the decompression phase) as ventilation will be more efficient and safer when the ventilation occurs when the intrathoracic pressure is negative such as during the decompression phase. In some versions, the synchronization may be accomplished based on feedback provided to the rescuer such as a prompt that indicates when a ventilation is to start and stop. That is, when a transition point is detected such that the system determines that non-elevated decompression is beginning, the system may provide a prompt to a user and/or machine to initiate a positive pressure ventilation breath. For example, the synchronization may be accomplished based on an output to a mechanical ventilation unit that indicates which of the phases an inspiratory ventilation cycle can occur.

Figure 7A:
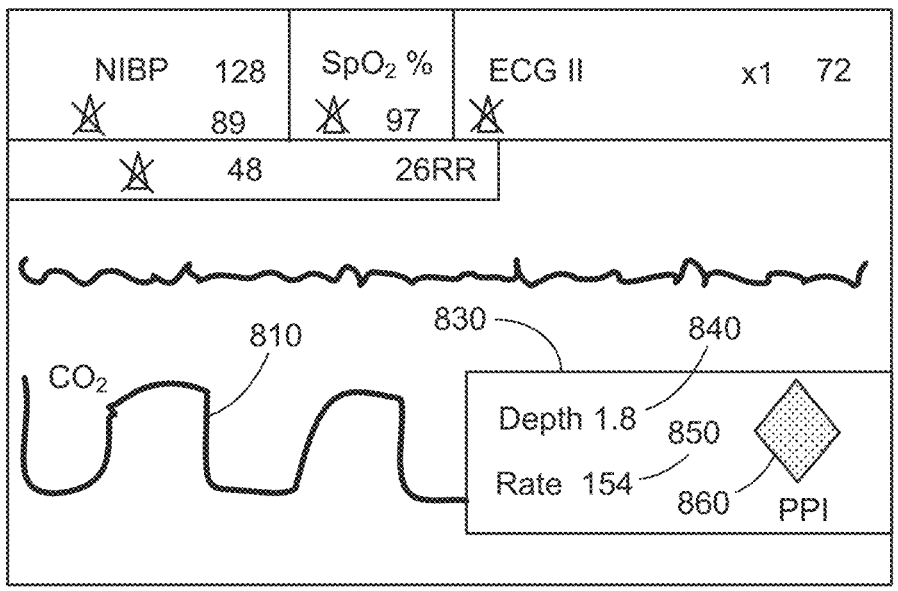
FIGS. 7A-7C show screenshots of an ACD Resuscitation device display that provides feedback concerning chest compressions performed on a patient.
Figure 7B:
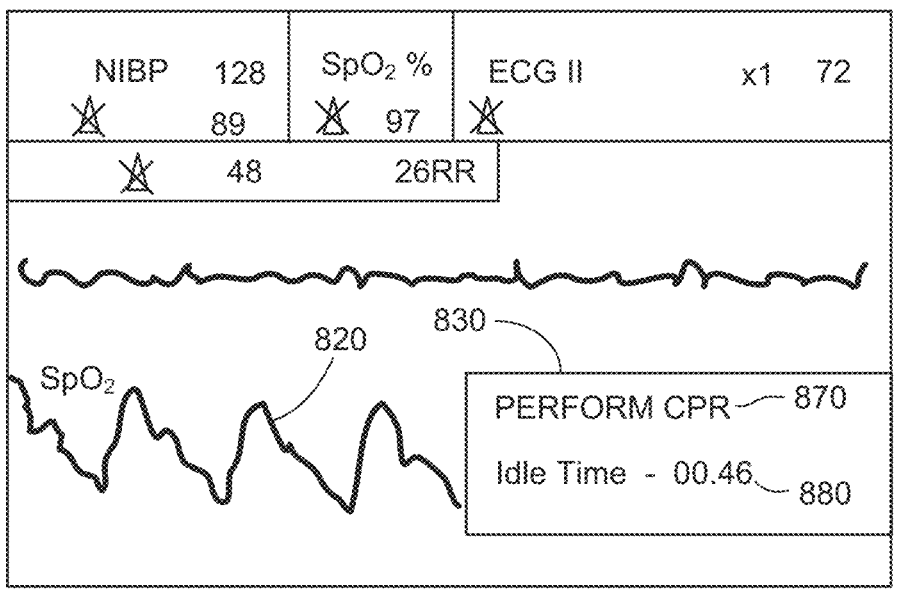
Figure 7C:
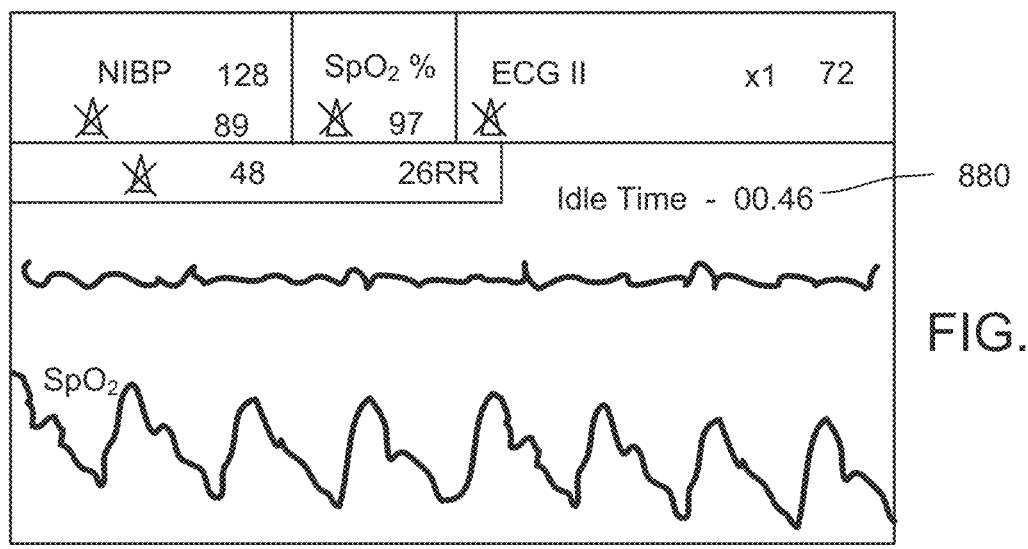

FIGS. 7A-7C show example screens that can be displayed on an ACD Resuscitation device, such as on display 630 of ACD Resuscitation device 600 of FIG. 3B. FIG. 7A shows exemplary data displayed during the administration of CPR chest compressions and decompressions, while FIGS. 7B and 7C show exemplary data displayed when CPR chest compressions and decompressions are not being sensed by the ACD Resuscitation device 600. The ACD Resuscitation device 600 dynamically switches what data is presented based on data received from one or more sensors, such as based on whether chest compressions and decompressions are detected by an accelerometer. An exemplary modification of the data presented on the display can include automatically switching one or more waveforms that the defibrillator displays. In one example, the type of measurement (e.g., waveform) displayed can be modified based on the presence or absence of chest compressions and decompressions. For example, $CO_2$ or depth of chest compressions and decompressions can be displayed (e.g., a $CO_2$ waveform 810 is displayed in FIG. 7A) during CPR administration, and upon detection of the cessation of chest compressions and decompressions, the waveform can be switched to display a $SpO_2$ or pulse waveform (e.g., a $SpO_2$ waveform 820 is displayed in FIG. 7B).

Another exemplary modification of the data presented on the display can include automatically adding/removing the CPR data from the display upon detection of the presence or absence of chest compressions and decompressions. As shown in FIG. 7A, when chest compressions and decompressions are detected, a portion 830 of the display includes data about the CPR such as depth 840, rate 850, and PPI 860. As shown in FIG. 7B, when CPR is halted and the system detects the absence of CPR chest compressions and decompressions, the defibrillator changes the CPR data in the portion 830 of the display, to include an indication 870 that the rescuer should resume CPR, and an indication 880 of the idle time since chest compressions and decompressions were last detected. In a similar manner, when the defibrillator determines that rescuers should change, the indication 870 can change to a message such as "Change Who is Administering CPR." In some implementations, as shown in FIG. 7C, when CPR is halted, the defibrillation device can remove the portion 830 of the display previously showing CPR data and can display a larger or extended view of one or more of the waveforms, such as waveforms 810, 820. Additionally, as shown by FIG. 7C, data about the idle time can be presented on another portion of the display.

Figure 8A:
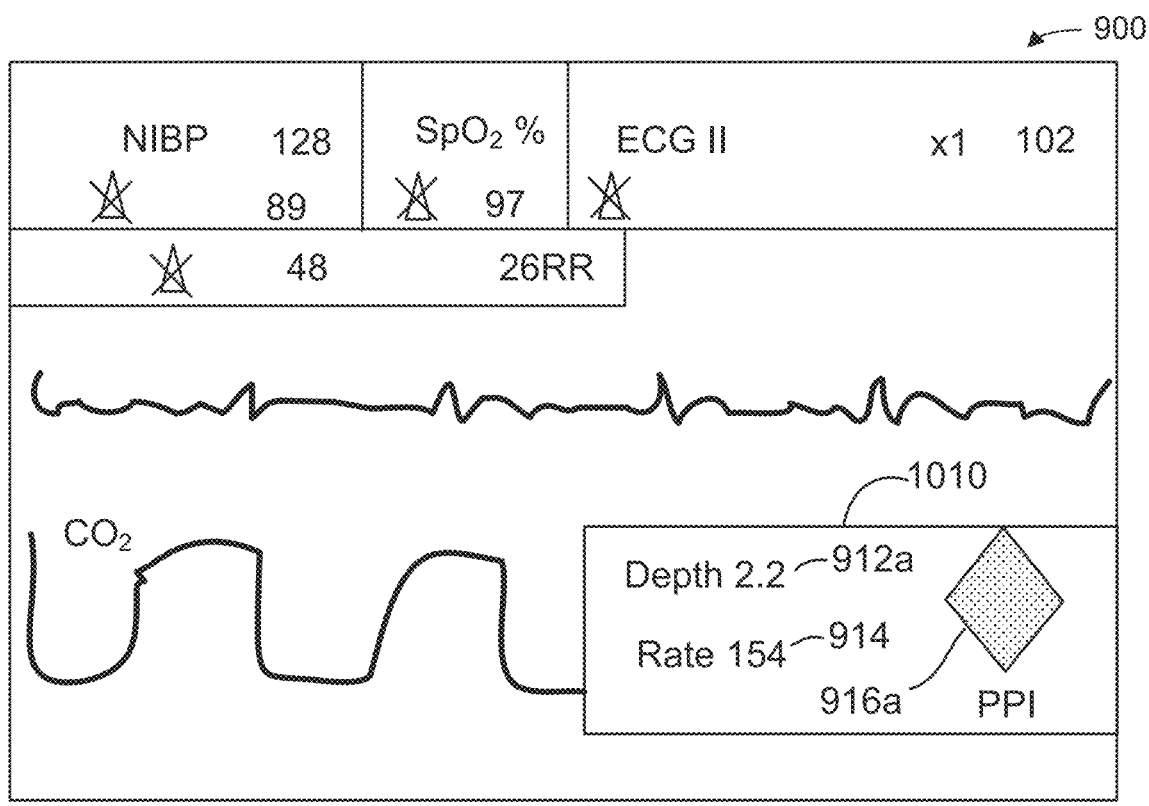
FIGS. 8A and 8B show screenshots providing feedback regarding a perfusion index created form chest compressions using the ACD Resuscitation device.
Figure 8B:
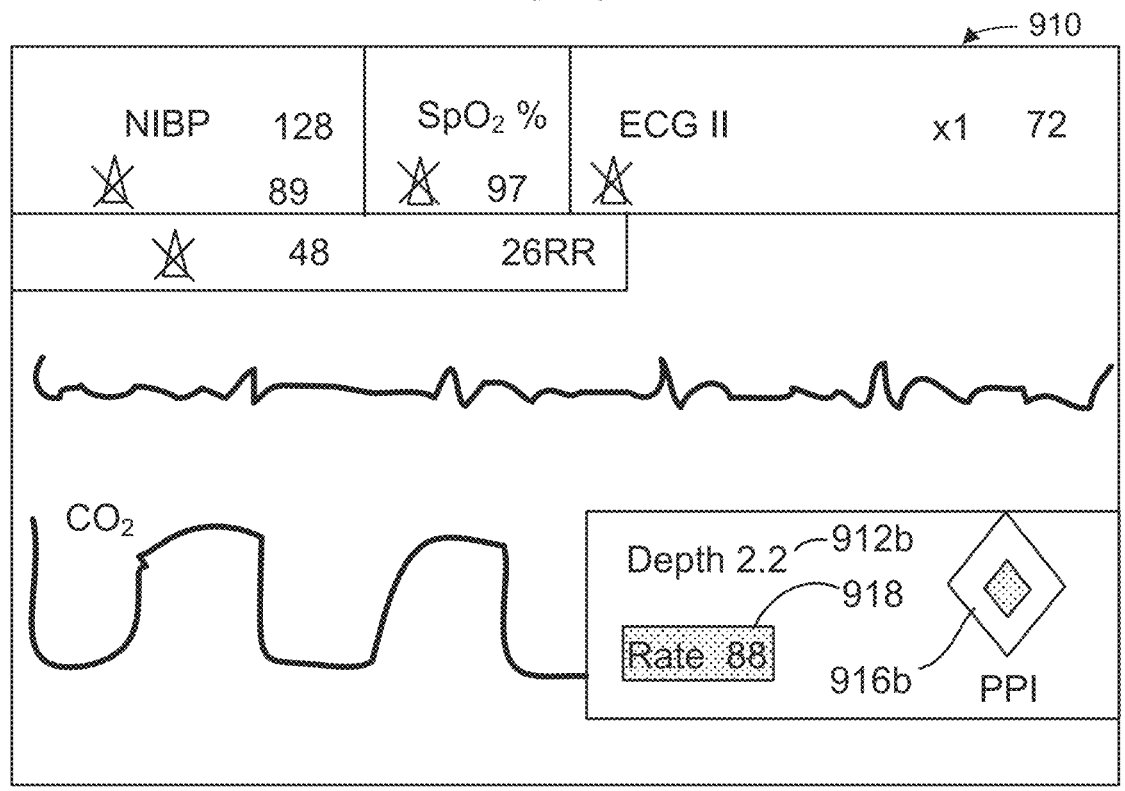

FIGS. 8A and 8B show example display screens of an ACD Resuscitation device (e.g., ACD Resuscitation device 600 of FIG. 3B). The displays 900, 910 indicate levels of perfusion being obtained by chest compressions and decompressions that the rescuer is performing. FIG. 8A shows exemplary data displayed during the administration of CPR chest compressions and decompressions when the CPR quality is within acceptable ranges, while FIG. 8B shows modifications to the display when the CPR quality is outside of the acceptable range.

In the example shown in FIG. 8B, the rate 914 of chest compressions and decompressions has dropped from 154 compressions and decompressions per minute (FIG. 8A) to 88 compressions and decompressions per minute (shown by visual indication 918 of FIG. 8B). The ACD Resuscitation device 200 determines that the compression rate of 88 compressions and decompressions per minute is below the acceptable range of greater than 100 compressions and decompressions per minute. In order to alert the user that the compression rate has fallen below the acceptable range, the ACD Resuscitation device 200 provides the visual indication 918 to emphasize the rate data. In this example, the visual indication 918 is a highlighting of the rate data. Similar visual indications can be provided based on depth measurements 912a, 912b when the depth of the compressions and decompressions is shallower or deeper than an acceptable range of depths. Also, when the change in rate or depth indicates that a rescuer is becoming fatigued, the system can display a message to switch who is performing the chest compressions and decompressions, and can also emit aural or haptic feedback to the same effect.

In the examples shown in FIGS. 8A and 8B, perfusion performance indicators (PPIs) 916a, 916b provide additional data about the quality of chest compressions and decompressions during CPR treatment. The PPIs 916a, 916b each include a shape (e.g., a diamond) with the amount of fill in the shape differing based on the measured rate and depth of the compressions and decompressions. In FIG. 8A, the depth and rate fall within the acceptable ranges (e.g., 100-120 compressions and decompressions/minute (CPM) and the depth of each compression being between 2-2.4 inches) so the PPI indicator 916a shows a fully filled shape. In contrast, in FIG. 8B, when the rate has fallen below the acceptable range, the amount of fill in the PPI indicator 916b is lessened such that only a portion of the indicator is filled. The partially filled PPI 916b provides a visual indication of the quality of the CPR is below an acceptable range. It can be appreciated that other target ranges for the rate and depth of compressions and decompressions may be employed. For example, in some cases, a preferred rate of compressions and decompressions is between 80-100 compressions and decompressions per minute.

As noted above with respect to FIG. 6, in addition to measuring data about the rate and depth of CPR chest compressions and decompressions, in some implementations the ACD Resuscitation device 200 may provide further data about the active decompression portion of the applied CPR. For example, as a rescuer tires, the rescuer may have a tendency to lean on the patient between chest compressions and decompressions such that the chest cavity is not able to fully expand at the end of a compression. If the rescuer does not properly perform (portions of) chest compressions and/or decompressions the quality of the CPR can diminish. As such, providing a visual or audio indication to the user when the user does not fully release can be beneficial. In addition, such factors can be included in a determination of whether the rescuer's performance has deteriorated to a level that the rescuer should be instructed to permit someone else perform the chest compressions and decompressions, and such data can be conveyed in the various manners discussed above.

Figure 9A:
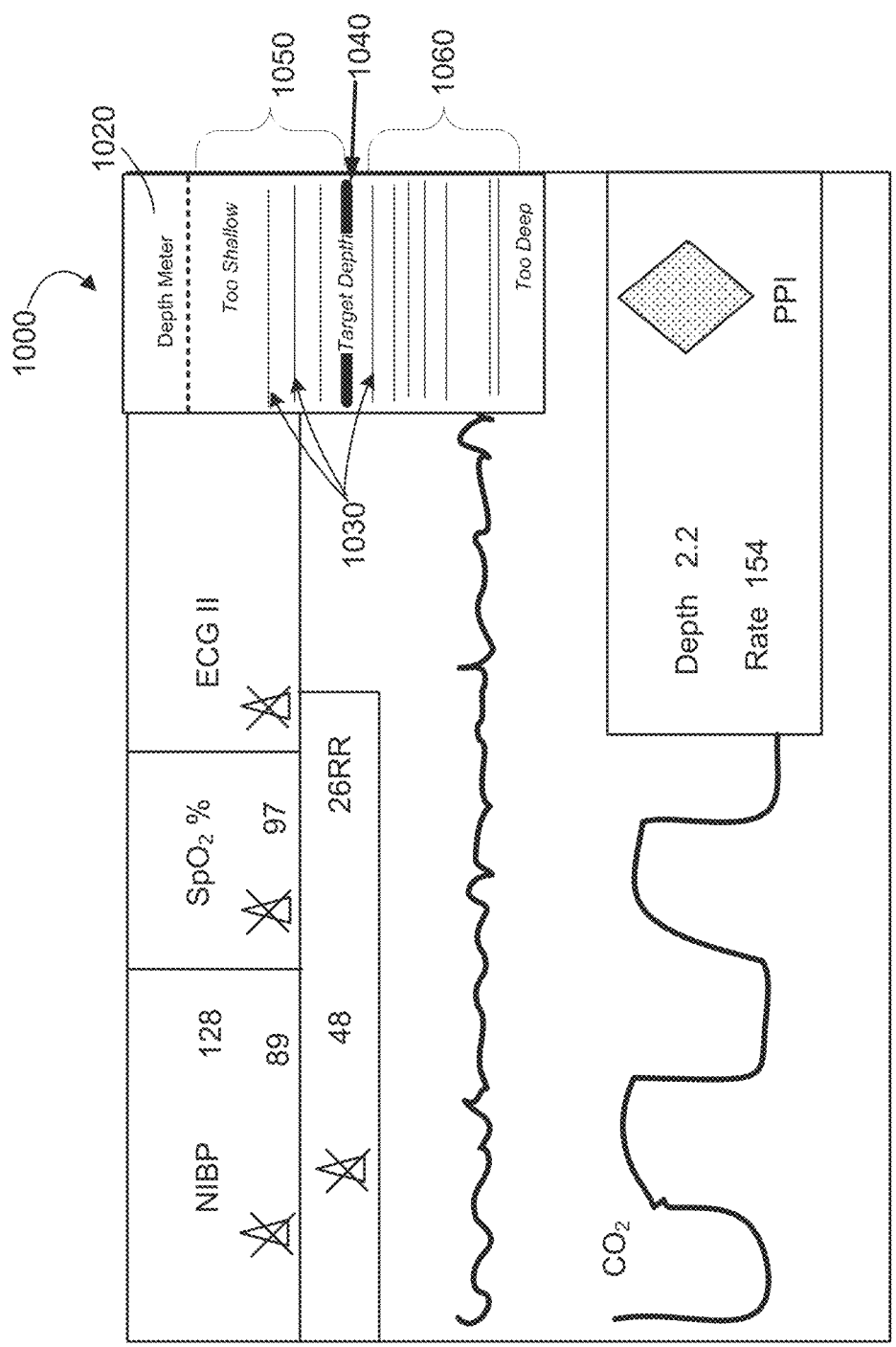
FIGS. 9A and 9B show screenshots of an ACD Resuscitation device that include graduated scales indicating target chest compression depths.
Figure 9B:
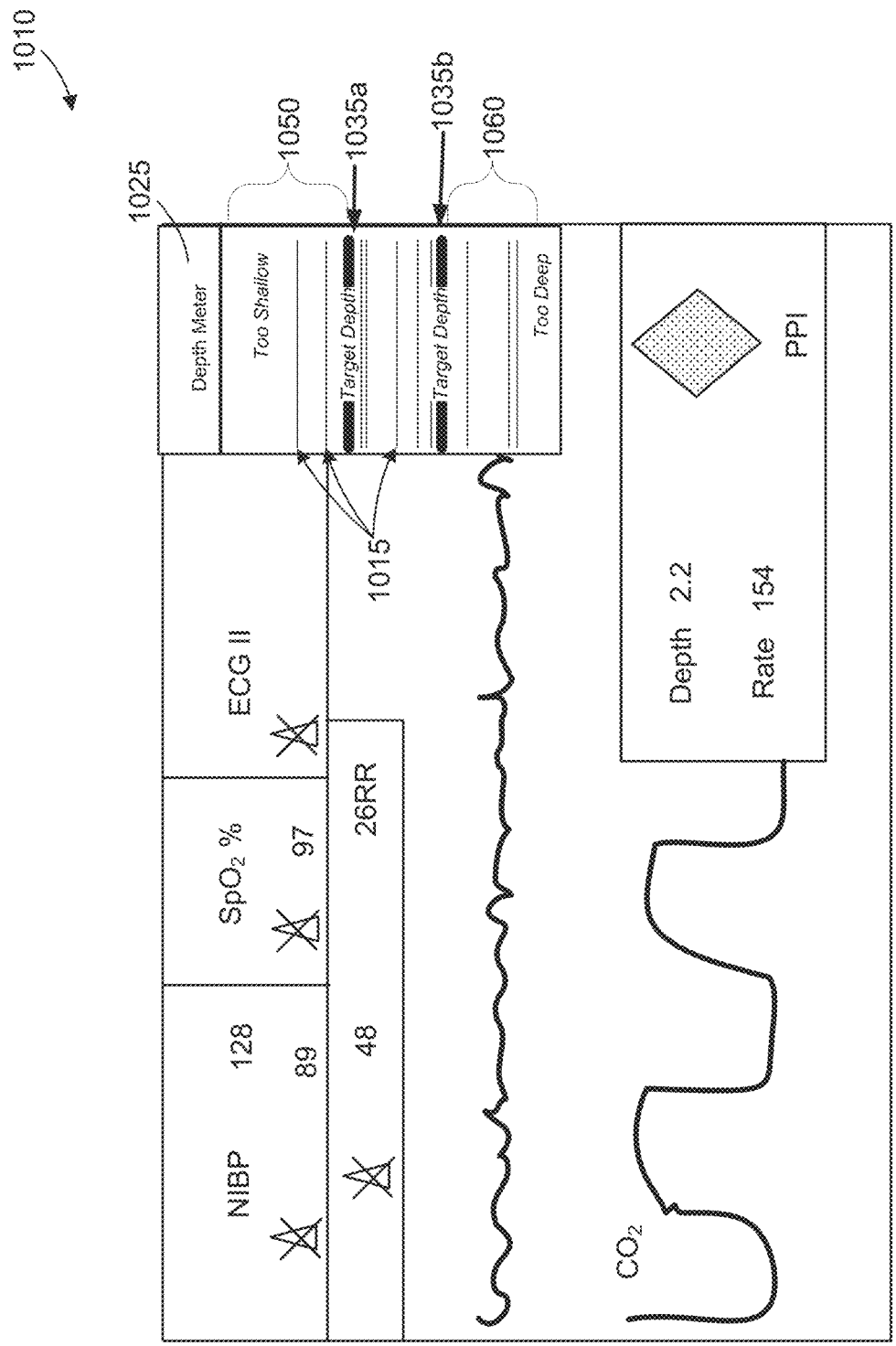

FIGS. 9A and 9B show example screens 1000, 1010, such as of ACD Resuscitation devices described herein. The screens 1000, 1010 depict visual representations of CPR quality being performed by a rescuer. As shown in FIG. 9A, a visual representation of CPR quality can include an indicator of CPR compression depth such as a CPR depth meter 1020. The CPR depth meter 1020 can be automatically displayed upon detection of CPR chest compressions and decompressions.

On the CPR depth meter 1020, depth bars 1030 visually indicate the depth of the administered CPR compressions and decompressions relative to a target depth 1040. As such, the relative location of the depth bars 1030 in relation to the target depth 1040 can serve as a guide to a rescuer for controlling the depth of CPR compressions and decompressions. For example, depth bars 1030 located in a region 1050 above the target depth bar 1040 indicate that the compressions and decompressions were shallower than the target depth, and depth bars 1030 located in a region 1060 below the target depth bar 1040 indicate that the compressions and decompressions were deeper than the target depth.

FIG. 9B shows an example screen 1010 including a depth meter 1025. While the example shown in FIG. 9A displayed the target depth 1040 as a single bar, in some additional examples, the target depth can be displayed as a range of preferred depths. For example, two bars 1035a and 1035b can be included on the depth meter 1025 providing an acceptable range of compression depths (e.g., as shown in FIG. 9B) and an acceptable amplitude of decompression. Additionally, in some implementations, compressions and decompressions that have amplitudes outside of an acceptable range can be highlighted in a different color than compressions and decompressions that have depths within the acceptable range of compression depths.

The depth bars 1015 displayed on the CPR depth meter 1025 can represent the compression depths of the most recent CPR compressions and decompressions administered by the rescuer. For example, the CPR depth meter 1025 can display depth bars 1015 for the most recent 10-20 CPR compressions and decompressions (e.g., the most recent 10 CPR compressions and decompressions, the most recent 15 compressions and decompressions, the most recent 20 CPR compressions and decompressions). In another example, CPR depth meter 1025 can display depth bars 1015 for CPR compressions and decompressions administered during a particular time interval (e.g., the previous 10 seconds, the previous 20 seconds).

In some additional embodiments, physiological data (e.g., physiological data such as end-tidal $CO_2$ data, arterial pressure data, volumetric $CO_2$, pulse oximetry (presence of amplitude of waveform possibly), carotid blood flow (measured by Doppler) of the patient (and in some cases, the rescuer), amongst other types of data can be used to provide feedback on the effectiveness of the CPR delivered at a particular target depth. Based on the physiological data, the system can automatically determine a target CPR compression depth (e.g., calculate or look-up a new CPR compression target depth) and, for example, provide feedback to a rescuer to increase or decrease the depth/rate of the CPR compressions and decompressions. Such feedback can include a sequence of desirable positions to guide the rescuer to adjust his/her body position and/or body motion to achieve a desirable combination of CPR compressions and decompressions (e.g., depth, rate), rescuer fatigue, and/or physiological outcome. Thus, the system can provide both feedback related to how consistently a rescuer is administering CPR compressions and decompressions at a target depth/rate, and feedback related to whether the target depth/rate should be adjusted based on measured physiological parameters, along with how the rescuer may enhance his/her body positioning in administering CPR treatment. If the rescuer does not respond to such feedback and continues to perform sub-optimal CPR, the system can then display an additional message to switch out the person performing CPR chest compressions and decompressions.

In some implementations, the system regularly monitors and adjusts the target CPR compression depth. In order to determine a desirable target depth, the system makes minor adjustments to the target CPR compression depth and observes how the change in compression depth affects the observed physiological parameters before determining whether to make further adjustments to the target compression depth. More particularly, the system can determine an adjustment in the target compression depth that is a fraction of an inch or a centimeter and prompt the rescuer to increase or decrease the compression depth by the determined amount. For example, the system can adjust the target compression depth by 2.5-10 mm (e.g., 2.5 mm to 5 mm or about 5 mm) and provide feedback to the rescuer about the observed compression depth based on the adjusted target compression depth. Then, over a set period of time, the system can observe the physiological parameters and, based on trends in the physiological parameters without making further adjustments to the target compression depth and at the end of the set time period, can determine whether to make further adjustments to the target compression depth.

The actual performance of the rescuer against the revised target can be continually monitored to determine when the rescuer's performance has fallen below an acceptable level, so that the rescuer and perhaps others can be notified to change who is performing the chest compressions and decompressions. Also, each of the relevant parameters of patient condition discussed above with respect to the various screenshots can be made one of multiple inputs to a process for determining when rescuers who are performing one component of a rescue technique should be switched out with another rescuer, such as for reasons of apparent fatigue on the part of the first rescuer.

The described techniques can be assisted by the use of a computer-implemented medical device, such as an ACD Resuscitation device having defibrillator components that includes computing capability. Such defibrillator or other device is shown and described herein, and can communicate with and/or incorporate a computer system 1100 in performing the operations discussed above, including operations for computing the quality of one or more components of CPR provided to a patient and generating feedback to rescuers, including feedback to change rescuers who are performing some components of the CPR treatment. The system 1100 can be implemented in various forms of digital computers, including computerized defibrillators laptops, personal digital assistants, tablets, and other appropriate computers. Additionally, the system can include portable storage media, such as, Universal Serial Bus (USB) flash drives. For example, the USB flash drives can store operating systems and other applications. The USB flash drives can include input/output components, such as a wireless transmitter or USB connector that can be inserted into a USB port of another computing device.

The system 1100 includes a processor 1110, a memory 1120, a storage device 1130, and an input/output device 1140. Each of the components 1110, 1120, 1130, and 1140 are interconnected using a system bus 1150. The processor 1110 is capable of processing instructions for execution within the system 1100. The processor can be designed using any of a number of architectures. For example, the processor 1110 can be a CISC (Complex Instruction Set Computers) processor, a RISC (Reduced Instruction Set Computer) processor, or a MISC (Minimal Instruction Set Computer) processor.

In one implementation, the processor 1110 is a single-threaded processor. In another implementation, the processor 1110 is a multi-threaded processor. The processor 1110 is capable of processing instructions stored in the memory 1120 or on the storage device 1130 to display graphical data for a user interface on the input/output device 1140.

The memory 1120 stores data within the system 1100. In one implementation, the memory 1120 is a computer-readable medium. In one implementation, the memory 1120 is a volatile memory unit. In another implementation, the memory 1120 is a non-volatile memory unit.

The storage device 1130 is capable of providing mass storage for the system 1100. In one implementation, the storage device 1130 is a computer-readable medium. In various different implementations, the storage device 1130 can be a floppy disk device, a hard disk device, an optical disk device, or a tape device.

The input/output device 1140 provides input/output operations for the system 1100. In one implementation, the input/output device 1140 includes a keyboard and/or pointing device. In another implementation, the input/output device 1140 includes a display unit for displaying graphical user interfaces.

The features described can be implemented in digital electronic circuitry, or in computer hardware, firmware, software, or in combinations of them. The apparatus can be implemented in a computer program product tangibly embodied in a data carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform some activity or bring about some result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semi-conductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having an LCD (liquid crystal display) or LED display for displaying data to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network (e.g., network 130). Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network (e.g., network 130). The relationship of client and server arises by virtue of computer programs running on the respective computers and having a client-server relationship to each other. Many other implementations other than those described can be employed, and can be encompassed by the following claims.

What is claimed is:

1. A medical apparatus for providing resuscitative therapy to a patient,
the apparatus comprising:
an electrocardiogram (ECG) input configured to receive an ECG signal of the patient;
a defibrillation output configured to provide an electrical defibrillation shock treatment to the patient; and
an applicator body coupled with the ECG input and the defibrillation output, the applicator body being configured to provide active compression decompression therapy to the patient, the applicator body comprising:
a rescuer end configured to enable a user to press and pull on the applicator body,
a coupling mechanism configured to couple to the patient to provide active compression decompression therapy as the user presses and pulls on the applicator body,
at least one capacitor configured to store charge for applying a defibrillation shock treatment to the patient, and
one or more processors configured to:
receive the ECG signal of the patient from the ECG input,
perform an analysis of the ECG signal of the patient to determine a cardiac-rhythm,
determine, based on the analysis of the ECG signal, whether the cardiac-rhythm is shockable, and
administer the defibrillation shock treatment to the patient via the defibrillation output based on a determination of whether the cardiac rhythm is shockable.

2. The apparatus of claim 1, further comprising at least one chest compression sensor for monitoring one or more chest compression parameters.

3. The apparatus of claim 2, wherein the one or more chest compression parameters comprise at least one of a displacement parameter, a force parameter, and a velocity parameter.

4. The apparatus of claim 2, wherein the at least one chest compression sensor comprises at least one of a motion sensor and a force sensor.

5. The apparatus of claim 4, wherein the motion sensor comprises at least one of an accelerometer, a velocity sensor and a displacement sensor.

6. The apparatus of claim 1, further comprising at least one electrode configured to be coupled with the ECG input and adhered to at least a portion of the patient for monitoring the ECG of the patient.

7. The apparatus of claim 6, wherein the at least one electrode is configured to be coupled with the defibrillation output and transmit the defibrillation shock treatment to the patient from the at least one capacitor.

8. The apparatus of claim 1, further comprising at least one electrode being configured to be coupled with the defibrillation output and transmit the defibrillation shock treatment to the patient from the at least one capacitor.

9. The apparatus of claim 7, wherein the one or more processors are configured to determine whether the ECG signal comprises a shockable or non-shockable rhythm, and cause the at least one capacitor and the at least one electrode to apply the defibrillation shock treatment upon a determination that the ECG signal comprises a shockable rhythm.

10. The medical apparatus of claim 1, wherein the applicator body comprises an insulating material configured to electrically isolate a defibrillating shock of the defibrillation shock treatment.

11. The apparatus of claim 1, wherein the one or more processors are configured to detect chest compressions being administered to the patient.

12. The apparatus of claim 11, wherein the one or more processors are configured to transmit a feedback signal for assisting a user in administering the chest compressions.

13. The apparatus of claim 1, further comprising a user interface that provides, by an output device, one or more of cardio-pulmonary resuscitation (CPR) instructions and defibrillation instructions, wherein the instructions include treatment data from one or more sensors.

14. The apparatus of claim 7, wherein the at least one electrode is configured to deploy a conductive gel for being adhered to the portion of the patient.

15. The apparatus of claim 1, further comprising a deployable electrode configured to be adhered to a portion of a back of the patient.

16. The apparatus of claim 15, wherein the deployable electrode is configured to be deployed from the applicator body using a spring-loaded mechanism.

17. The apparatus of claim 15, wherein the deployable electrode comprises a semi-rigid plate electrode.

18. The medical apparatus of claim 1, wherein the coupling mechanism of the applicator body is configured to couple to the patient using one or more of an adhesive, one or more suction cups, and a gel.

19. The apparatus of claim 1, wherein the one or more processors are further configured to synchronize a defibrillating shock treatment with a chest compression cycle.

20. The medical apparatus of claim 1, wherein the applicator body includes a stem disposed between the rescuer end and the coupling mechanism, the stem housing the at least one capacitor.

21. The apparatus of claim 1, wherein the one or more processors are configured to communicate with a computing device including at least one of a tablet, a server, phone, a watch, laptop, and a mobile computing device.

22. The apparatus of claim 21, wherein the one or more processors are configured to transmit patient data to the computing device, the patient data including information indicative of at least one of the ECG signal and the defibrillation shock treatment.

23. The apparatus of claim 1, further comprising a user interface at the rescuer end, the user interface comprising a display and one or more controls for controlling the defibrillation shock treatment.

24. The apparatus of claim 23, wherein the display of the user interface is between a first and second handle of the rescuer end.

25. The apparatus of claim 23, wherein the user interface is configured to display real-time feedback of the active compression decompression therapy.

26. The apparatus of claim 23, wherein the user interface is configured to display an electrocardiogram waveform received via the electrocardiogram input.

27. The apparatus of claim 23, wherein the one or more processors are configured to determine when the active compression decompression therapy is being applied, and in response to determining, automatically cause the user interface to change a configuration.

28. The apparatus of claim 27, wherein the one or processors cause the user interface to change to a first configuration comprising display of a filtered ECG waveform when the active compression decompression therapy is being applied, and wherein the one or more processors cause the user interface to change to a second configuration comprising display of an unfiltered ECG waveform when the active compression decompression therapy is not being applied.

29. The apparatus of claim 23, wherein the user interface is configured to display one or more instructions for placement at least one of a coupling platform and one or more electrodes on the patient.

30. The apparatus of claim 23, wherein user interface is configured to display a reminder for the user to release pressure from the patient in response to a signal receiving by the one or more processors during active compression decompression therapy.

31. The apparatus of claim 23, wherein the user interface is configured to display at least one of a $CO_2$ waveform and an $SpO_2$ waveform during active compression decompression therapy.

32. The apparatus of claim 23, wherein the user interface is configured to display CPR instructions and CPR data during active compression decompression therapy, the CPR data comprising at least one of rate data, compression depth data, decompression depth data, and a perfusion performance indicator.

33. The medical apparatus of claim 1, wherein the coupling mechanism comprises at least one of a coupling surface, a plunger, a check valve, a compression pad, and a magnet assembly, the coupling surface coupling to a coupling platform adhered to the patient, the compression pad being configured to regulate force applied to the patient by the coupling mechanism, the magnet assembly being disposed on the applicator body, and the coupling surface being configured to actuate a compression sensor affixed to the patient during active compression decompression therapy.

34. The apparatus of claim 33, wherein the compression pad comprises one or more suction cups.

35. The apparatus of claim 33, wherein the compression pad comprises an adhesive layer.

36. The apparatus of claim 33, wherein the compression pad comprises increasing stiffness from edges of the compression pad toward a geometrical center of the compression pad.

37. The medical apparatus of claim 1, wherein the applicator body further comprises optoisolators configured to electrically insulate one or more portions of the applicator body.

38. The medical apparatus of claim 33, wherein a magnetic field of the magnet is focused by a magnetic core, a non-magnetic sleeve, and a ferromagnetic pot.

39. The apparatus of claim 1, wherein the defibrillation output and the ECG input comprise a shared physical port.

40. The apparatus of claim 1, wherein the defibrillation output comprises a first physical port, wherein the ECG input comprises a second physical port, and wherein the first physical port is different than the second physical port.

41. The medical apparatus of claim 1, further comprising a communications device configured to wirelessly communicate with a remote computing device.

42. The medical apparatus of claim 1, further comprising a handle at the rescuer end, wherein the handle comprises one or more of batteries, a user interface, a power supply, a defibrillator charge and switch, and the one or more processors.

43. The medical apparatus of claim 1, wherein the coupling mechanism comprises the defibrillation output.

44. The medical apparatus of claim 1, wherein the coupling mechanism comprises a breakaway mechanism.

45. The medical apparatus of claim 1, wherein one or both of the defibrillation output and the ECG input are affixed to the rescuer end of the applicator body.

46. The medical apparatus of claim 1, further comprising one or more electrodes that are configured to be stored in a rolled format near the applicator body.

* * * * *